(12) United States Patent
Slomczynska et al.

(10) Patent No.: US 8,263,568 B2
(45) Date of Patent: Sep. 11, 2012

(54) CHROMATOGRAPHY OF METAL COMPLEXES

(75) Inventors: Urszula J. Slomczynska, Ballwin, MO (US); Bobby N. Trawick, Florissant, MO (US); Dennis P. Riley, Chesterfield, MO (US); Arati Naik, St. Louis, MO (US)

(73) Assignee: Galera Therapeutics, LLC, St. Louis, MO (US)

( * ) Notice: Subject to any disclaimer, the term of this patent is extended or adjusted under 35 U.S.C. 154(b) by 0 days.

(21) Appl. No.: 12/787,260

(22) Filed: May 25, 2010

(65) Prior Publication Data

US 2010/0304415 A1 Dec. 2, 2010

Related U.S. Application Data

(63) Continuation of application No. 10/469,440, filed as application No. PCT/US02/06521 on Mar. 4, 2002, now abandoned.

(60) Provisional application No. 60/273,220, filed on Mar. 2, 2001.

(51) Int. Cl.
*A01N 43/04* (2006.01)

(52) U.S. Cl. .......................................................... 514/43

(58) Field of Classification Search .................. 436/101; 514/43
See application file for complete search history.

(56) References Cited

U.S. PATENT DOCUMENTS

| | | | |
|---|---|---|---|
| 5,610,293 A * | 3/1997 | Riley et al. | 540/474 |
| 5,637,578 A * | 6/1997 | Riley et al. | 514/186 |
| 6,084,093 A | 7/2000 | Riley et al. | |
| 6,177,419 B1 | 1/2001 | Campbell et al. | |
| 6,180,620 B1 | 1/2001 | Salvemini | |
| 6,214,817 B1 | 4/2001 | Riley et al. | |
| 6,916,799 B2 | 7/2005 | Fridovich et al. | |
| 7,407,645 B2 | 8/2008 | Neumann et al. | |
| 7,445,641 B1 | 11/2008 | Ornberg et al. | |
| 2002/0072512 A1 * | 6/2002 | Salvemini | 514/184 |
| 2004/0219138 A1 * | 11/2004 | Salvemini | 424/94.4 |

FOREIGN PATENT DOCUMENTS

| | | | |
|---|---|---|---|
| WO | WO 9528968 A1 * | 11/1995 | |
| WO | WO 9706830 A1 * | 2/1997 | |
| WO | WO 9858636 A1 * | 12/1998 | |
| WO | WO 0072893 A2 | 12/2000 | |
| WO | WO 0119823 A3 | 3/2001 | |
| WO | 03024434 A2 | 3/2003 | |

OTHER PUBLICATIONS

U.S. Appl. No. 60/254,405, filed Dec. 8, 2000. 79 pages.*
U.S. Appl. No. 09/398,120, filed Sep. 16, 1999. 124 pages.*

(Continued)

*Primary Examiner* — Bobby Ramdhanie
(74) *Attorney, Agent, or Firm* — Bryan Cave LLP

(57) ABSTRACT

A high performance liquid chromatography method to routinely and reproducibly detect and quantitate metal complexes is provided. The metal complexes used in the method of the invention can be different metal complexes, or they can be stereoisomers of the same metal complexes. The high performance liquid chromatography method of the present invention is suitable for the separation of diastereomers of the same metal complexes. Also provided is a chiral high performance liquid chromatography method to separate enantiomers of metal complexes. Superoxide dismutase mimetic compounds are also provided.

11 Claims, 11 Drawing Sheets

OTHER PUBLICATIONS

Berge, S. M.; Bighley, L. D.; Monkhouse, D. C. "Pharmaceutical Salts." Journal of Pharmaceutical Sciences, 1977, vol. 66, pp. 1-19.*

Salvemini, et al. "A Nonpeptidyl Mimic of Superoxide Dismutase with Therapeutic Activity in Rats." Science, 1999, vol. 286, pp. 304-306.

Salvemini, et al. "A Nonpeptidyl Mimic of Superoxide Dismutase with Therapeutic Activity in Rats." Science, 1999, vol. 286, Supplemental Material. 3 pages.

Tabata, et al. "Ion-Pair Extraction of Metalloporphyrins into Acetonitrile for Determination of Copper(II)." Anal. Chem. 1996, 68, pp. 758-762.

Mazzucotelli, et al. "Determination of trace amounts of Metalloprotein Species in Marine Mussel Samples by High Performance Liquid Chromatography with Inductively Coupled Plasma Atomic Emission Spectrometric Detection." Analyst. 1991, 116, pp. 605-608.

Furuya, et al. "Determination of Pheophytinatoiron(III) Chlorides by Reverse Phase High Performance Liquid Chromatography." Analytical Sciences, 3, 1987, pp. 353-357.

Zhang, et al. "Quantitative determination of SC-68328 in dog plasma using flow injection and tandem mass spectroscopy." 2000, 35, pp. 354-360.

Sakai, et al. "Liquid-Chromatographic Separation and Determination of Coproporphyrins I & III in Urine." Clinical Chemistry. 1983, 29/2, pp. 350-353.

Riley, et al. "Synthesis, Characterization, and Stability of Manganese(II) C-Substituted 1,4,7,10,13-Pentaazacyclopentadecane Complexes Exhibiting Superoxide Dismutase Activity." 1996, 35, pp. 5213-5231.

Riley, et al. "Toward the Rational Design of Superoxide Dismutase Mimics: Mechanistic Studies for the Elucidation of Substituent Effects on the Catalytic Activity of Macrocyclic Manganese(II) Complexes." J.A.C.S. 1997, 199, pp. 5522-6528.

European Patent Office, European Patent Search issued Aug. 5, 2011.

Riley, Dennis P., Functional Mimics of Superoxide Dismutase Enzymes as Therapeutic Agents, Chem. Rev., May 17, 1999, 2573-2587.

* cited by examiner

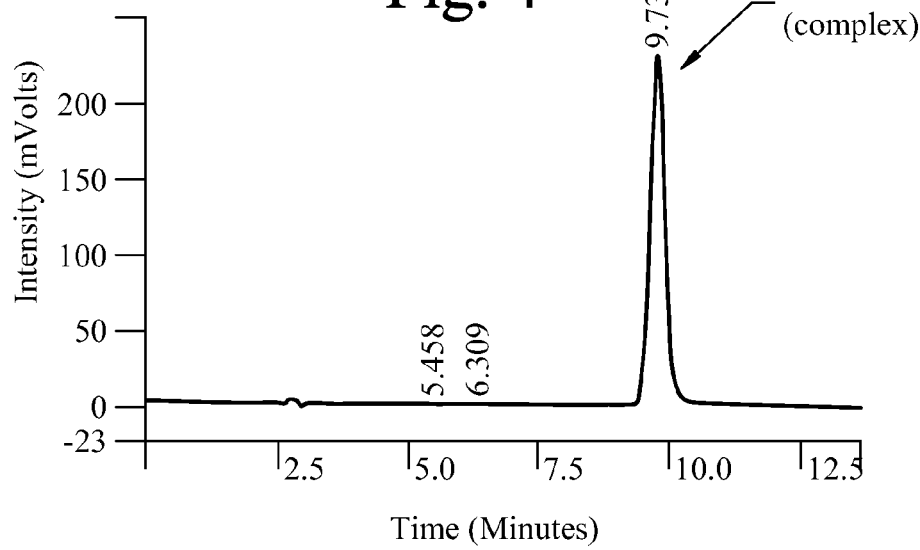
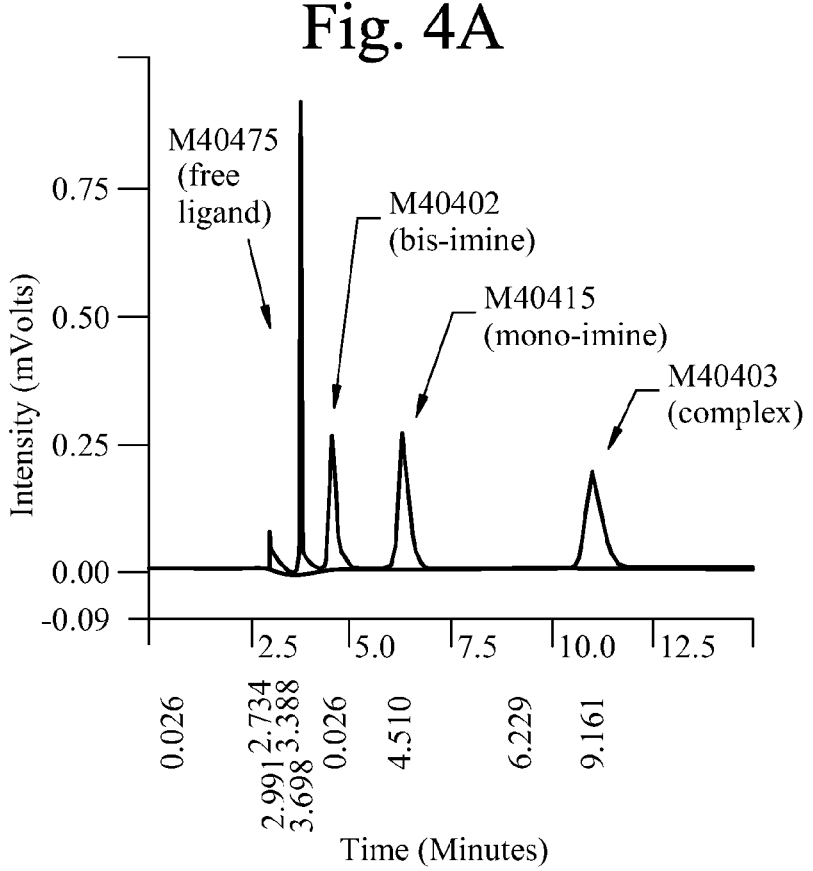

(A)

(Fig. 6 Continued)
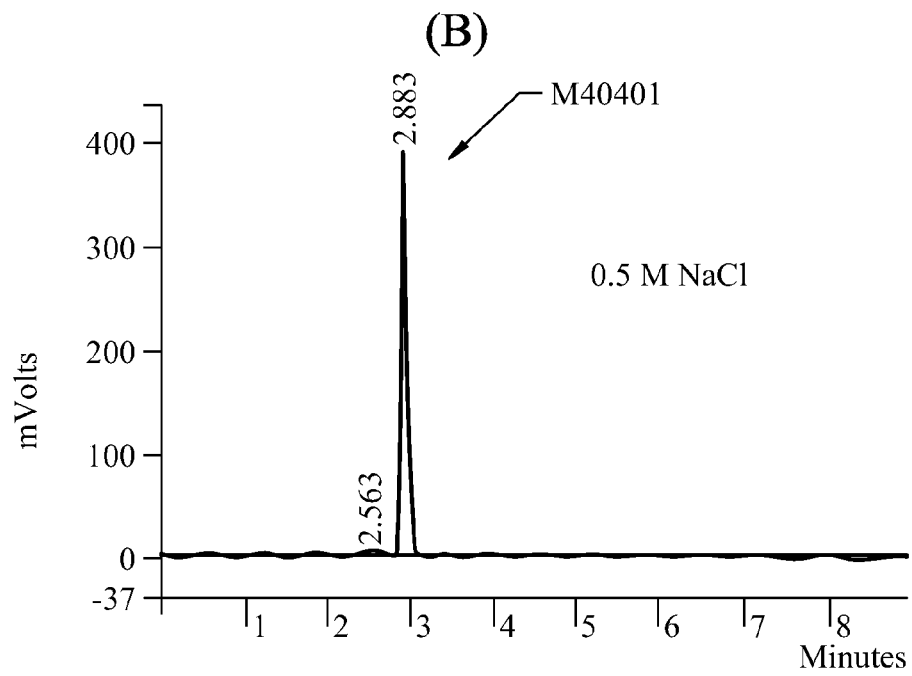
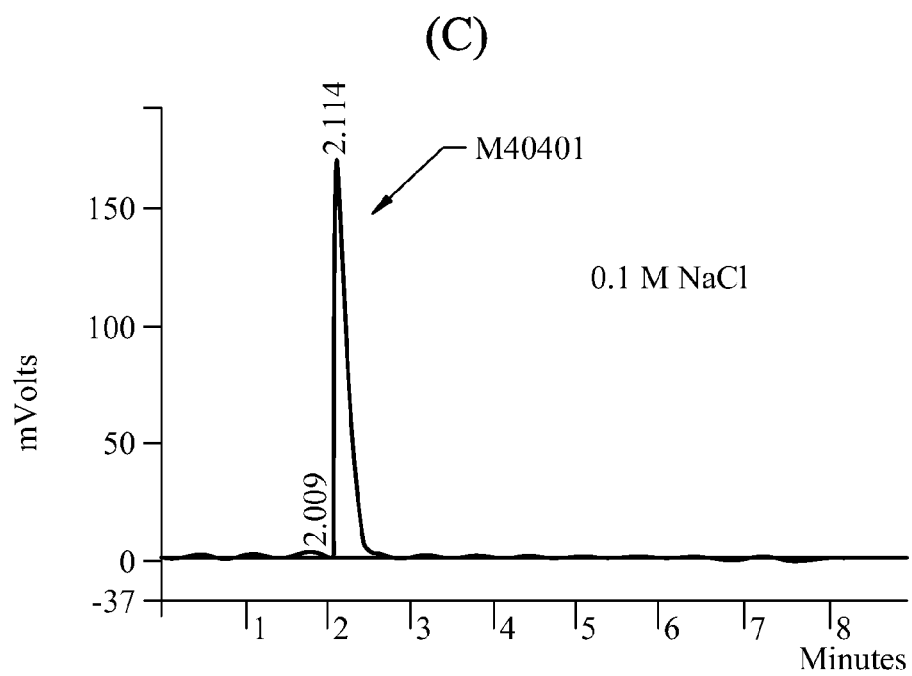

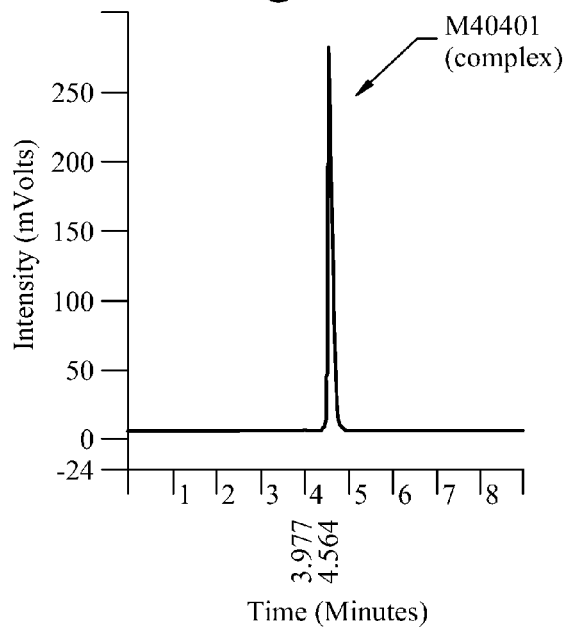
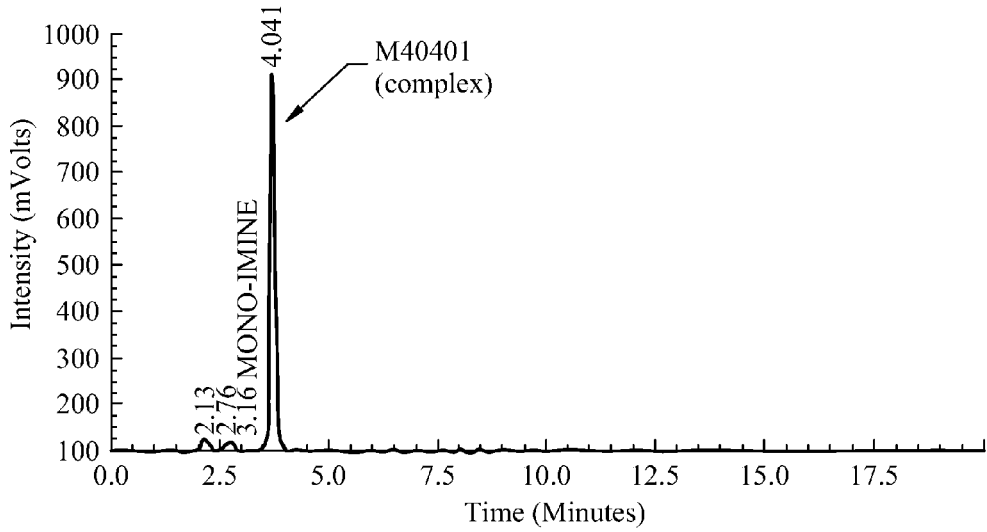

Fig. 12
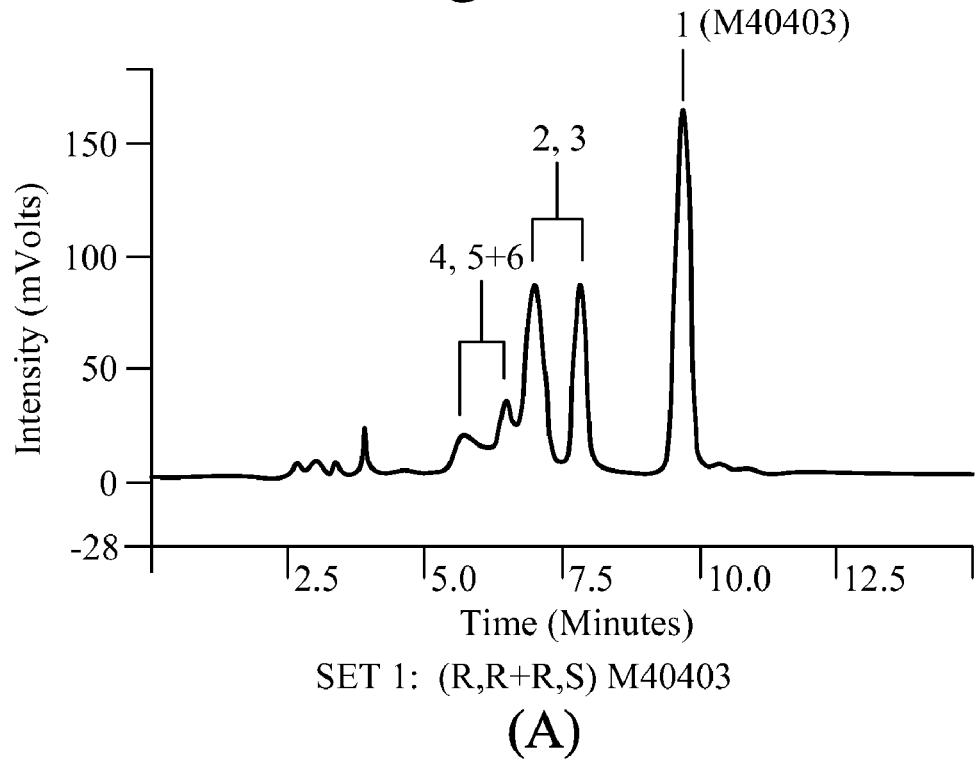
SET 1: (R,R+R,S) M40403
(A)
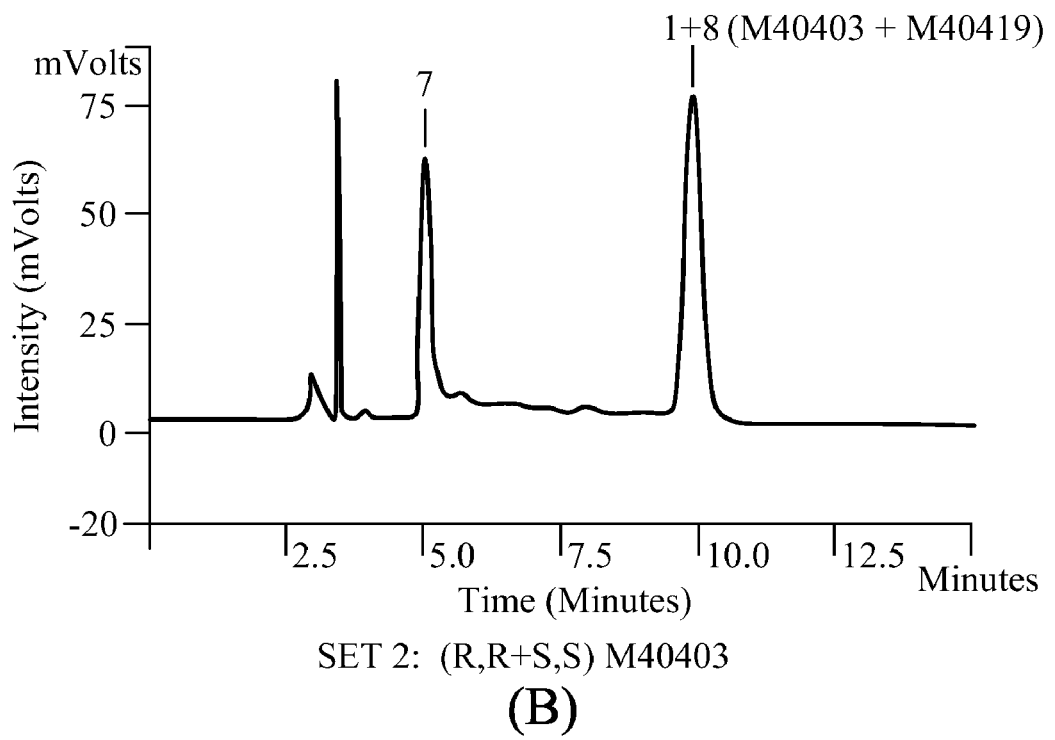
SET 2: (R,R+S,S) M40403
(B)

(Fig. 12 Continued)
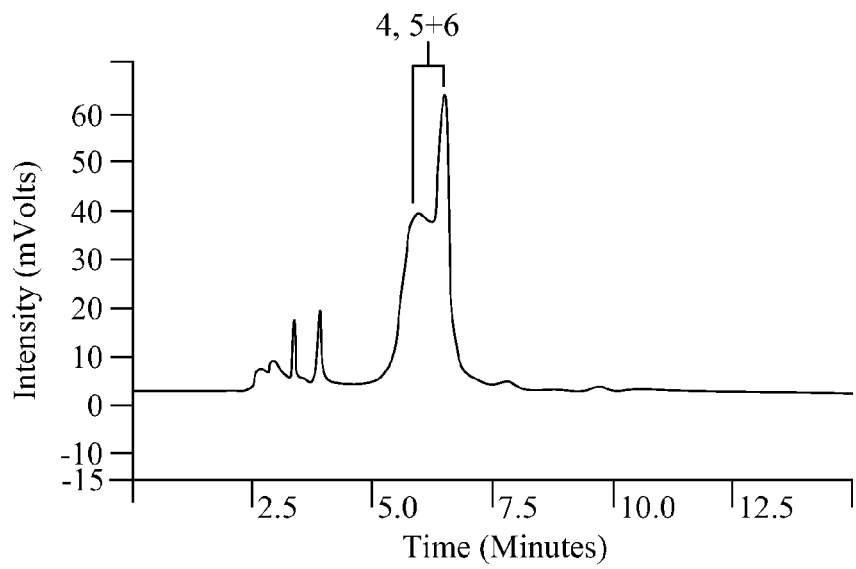
SET 3: (R,S+R,S) M40403
(C)
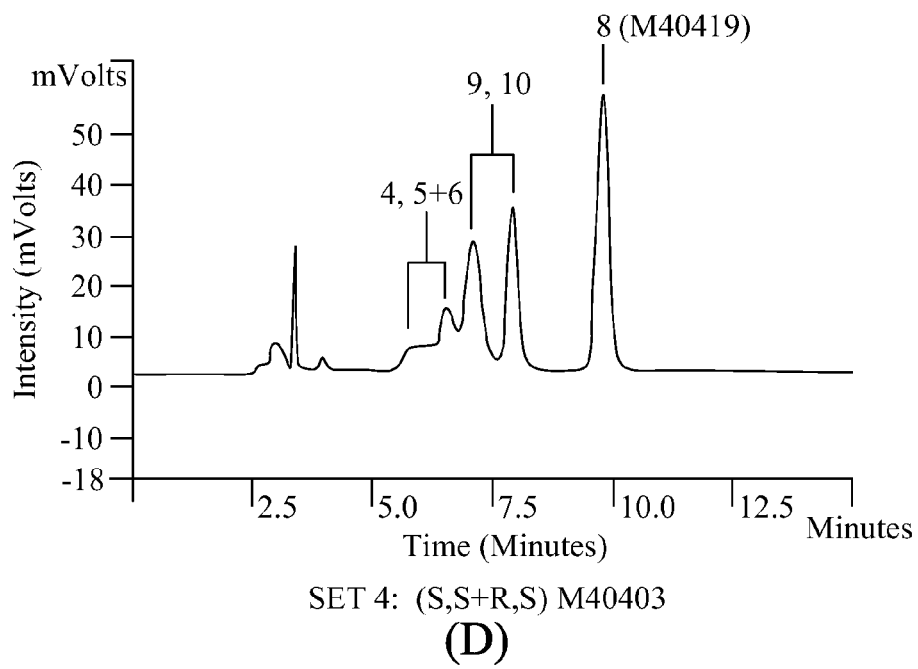
SET 4: (S,S+R,S) M40403
(D)

(Fig. 12 Continued)
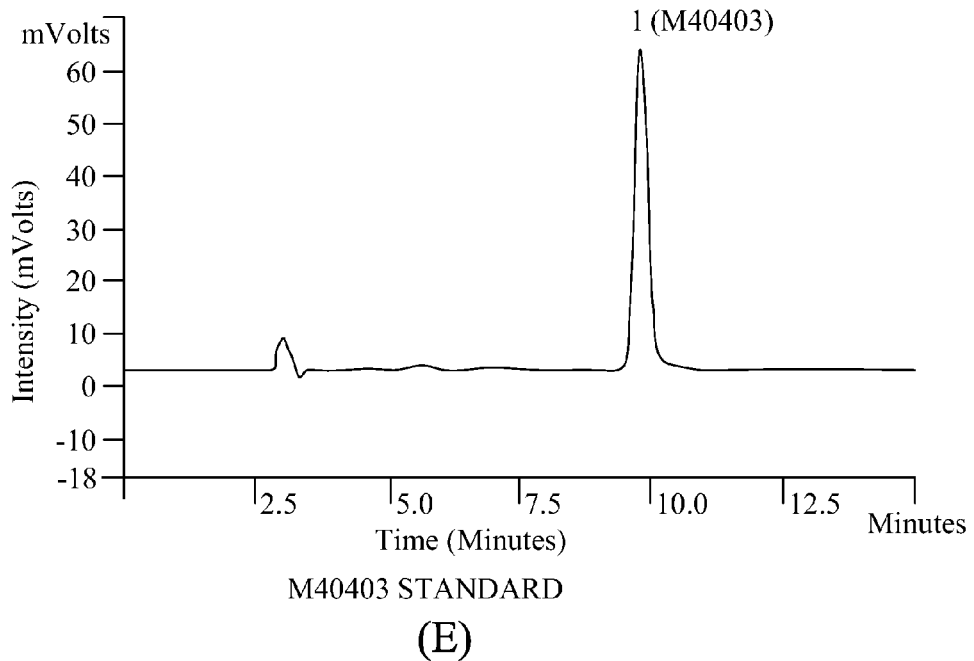
M40403 STANDARD
(E)
Fig. 13
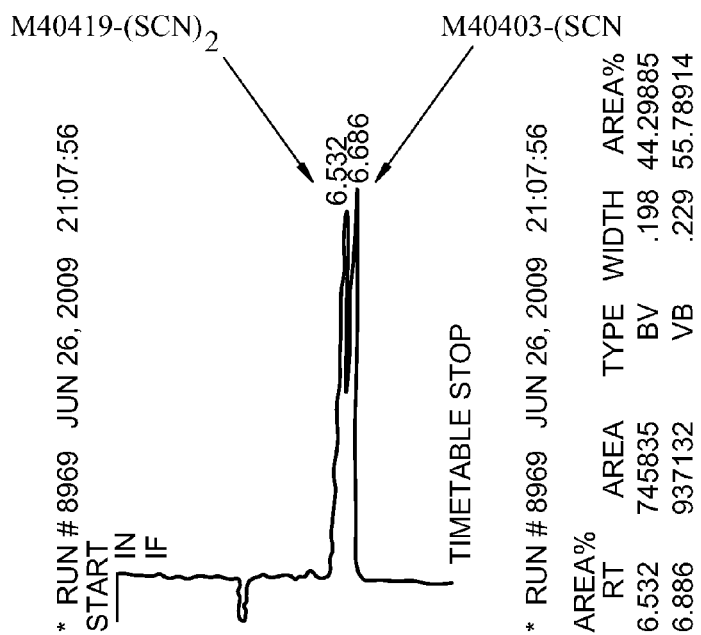

CHROMATOGRAPHY OF METAL COMPLEXES

CROSS-REFERENCE TO RELATED APPLICATIONS

This application is a continuation of U.S. Non-Provisional patent application Ser. No. 10/469,440 filed on Jan. 29, 2004, now abandoned, which was the National Stage of International Application No. PCT/US02/06521, filed Mar. 4, 2002, which claims priority from U.S. Provisional Patent Application Ser. No. 60/273,220 filed Mar. 2, 2001, each of which is incorporated herein by reference in its entirety.

FIELD OF THE INVENTION

This invention relates to a high performance liquid chromatography method for the analytical detection and quantification of metal complexes which have utility in pharmaceutical and diagnostic applications.

BACKGROUND OF THE INVENTION

Superoxide dismutase (SOD) enzymes are enzymes that catalyze the dismutation of the free radical superoxide, the one-electron reduction product of molecular oxygen. The dismutation of the free radical superoxide involves the conversion of this one-electron reduction product of molecular oxygen to the nonradical molecular oxygen. Superoxide dismutase enzymes are a class of oxidoreductases which contain either Cu/Zn, Fe, or Mn at the active site. Superoxide dismutase (SOD) mimetic compounds are low molecular weight catalysts which mimic the natural enzyme function of the superoxide dismutase enzymes. Thus, superoxide dismutase mimetic compounds also catalyze the conversion of superoxide into oxygen and hydrogen peroxide, rapidly eliminating the harmful biologically generated superoxide species that are believed to contribute to tissue pathology in a number of diseases and disorders. These diseases and disorders include reperfusion diseases, such as those following myocardial infarct or stroke, inflammatory disorders such as arthritis, and neurological disorders such as Parkinson's disease. *Chem Reviews*, 1999 vol 99, No. 9, 2573-2587.

Superoxide dismutase mimetic compounds possess several advantages over the superoxide dismutase enzymes themselves in that their chemical properties can be altered to enhance stability, activity and biodistribution while still possessing the ability to dismutase the harmful superoxide. Superoxide dismutase mimetic compounds have generated intense interest and have been the focus of considerable efforts to develop them as a therapeutic agent for the treatment of a wide range of diseases and disorders, including reperfusion injury, ischemic myocardium post-ischemic neuropathies, inflammation, organ transplantation and radiation induced injury. Most of the superoxide dismutase mimics currently being developed as therapeutic agents are synthetic low molecular weight manganese-based superoxide dismutase mimetic compounds. *Chem Reviews*, 2576.

Superoxide dismutase mimetic compounds are metal complexes in which the metal can coordinate axial ligands. Examples of such metal complexes include, but are not limited to, complexes of the metals Mn and Fe. Many of the complexes of the metals Mn and Fe do not possess superoxide dismutase activity but possess properties that enable them to be put to other therapeutic and diagnostic uses. These therapeutic and diagnostic uses include MRI imaging enhancement agents, peroxynitrite decomposition catalysts, and catalase mimics. These metal complexes, however, share the structural similarity of possessing a metal that can coordinate exchangeable ligands. These metal complexes exist in water as a mixture of species in which various ligands are possible. An illustration of such a mixture is provided by M40403, a Mn(II) complex of a nitrogen-containing fifteen membered macrocyclic ligand, shown in Scheme 1. One of the forms for this metal complex is the dichloro complex, which when dissolved in water another form is generated where one of the chloride anions immediately dissociates from the metal generating the [Mn(Cl)(aquo)]+complex. The problem in aqueous solvent systems or any solvent which has a potential donor atom is that there are a variety of potential ligands available to coordinate axially to the Mn(II) ion of the complex. In conducting an analysis of a sample containing a metal complex by high performance liquid chromatography (HPLC) the chromatogram tends to be very broad and unresolved due to the presence of the various species of complexes, as shown in Scheme 1. This phenomena makes the identification and quantification of metal complexes by standard HPLC techniques quite difficult. Therefore, in light of the developing roles of metal complexes as therapeutics in the treatment of various disorders and diagnostic agents, a substantial need exists for an effective and workable high performance liquid chromatography method for analyzing metal complexes.

Scheme 1

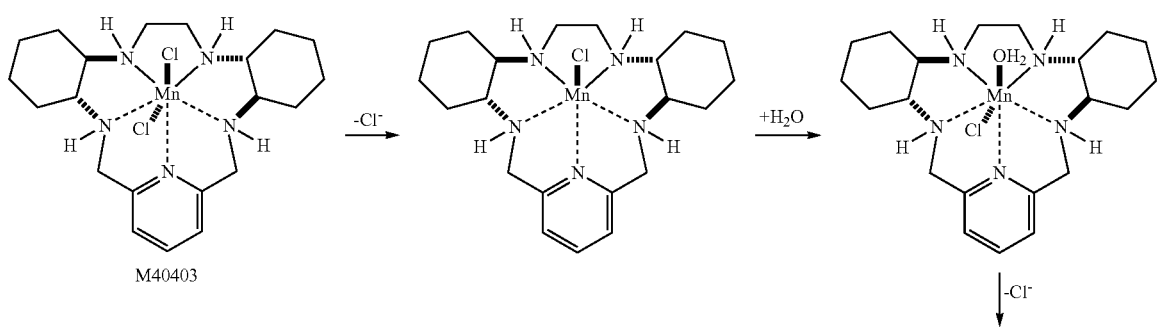

M40403

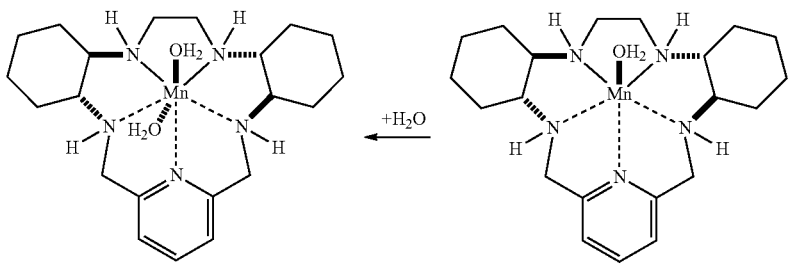

An additional complication which exists is the issue of the acid stability of the metal complex. As the pH decreases, the rate at which the complex becomes protonated and experiences instability increases. This presents particular problems for the use of HPLC as a method of detection and quantification of the metal complexes because the mobile phase used for reverse phase HPLC frequently contains mixtures of organic solvents and water in various combinations with trifluoroacetic acid. The trifluoroacetic acid is commonly present between about 0.1 to about 0.5% by weight. The presence of the trifluoroacetic acid causes the complex to dissociate. This dissociation destroys the potential of any such method to be used for release testing for purity. Furthermore, the trifluoroacetate anion causes the formation of some of the trifluoroacetato complex which could possess a different retention time from the chloro complexes thus, confusing the chromatography. Thus, the phenomenon of ligand exchange, coupled with the acid instability of the metal complexes, provides considerable challenges to the effort to detect and quantify metal complexes using HPLC. These challenges and needs have surprisingly been met by the invention described below.

Analytical HPLC is a powerful method to obtain information about a sample compound including information regarding identification, quantification and resolution of a compound. HPLC has been used particularly for the analysis of larger compounds and for the analysis of inorganic ions for which liquid chromatography is unsuitable. Skoog, D. A., West, M. A., *Analytical Chemistry*, 1986, p. 520. As an analytical tool HPLC takes advantage of the differences in affinity that a particular compound of interest has for the stationary phase and the mobile phase (the solvent being continuously applied to the column). Those compounds having stronger interactions with the mobile phase than with the stationary phase will elute from the column faster and thus have a shorter retention time. The mobile phase can be altered in order to manipulate the interactions of the target compound and the stationary phase. In normal-phase HPLC the stationary phase is polar, such as silica, and the mobile phase is a nonpolar solvent such as hexane or isopropyl ether. In reversed-phase HPLC the stationary phase is non-polar, often a hydrocarbon, and the mobile phase is a relatively polar solvent. Since 1974 when reversed-phase packing materials became commercially available, the number of applications for reversed-phase HPLC has grown, and reversed-phase HPLC is now the most widely used type of HPLC. Reversed-phase HPLC's popularity can be attributed to its ability to separate a wide variety of organic compounds. Reversed-phase chromatography is especially useful in separating the related components of reaction mixtures, and therefore is a useful analytical tool for determining the various compounds produced by reactions.

To create a non-polar stationary phase silica or synthetic polymer based adsorbents are modified with hydrocarbons. The most popular bonded phases are C1, C4, C8 and C18. Silica based adsorbents modified with trimethylchlorosilane (C1) and butyldimethylchlorosilane (C4) have a few applications in HPLC, mainly for protein separation or purification. These adsorbents show significant polar interactions. Octyl (C8) and octadecyl (C18) modified adsorbents are the most widely used silica based adsorbents, with almost 80% of all HPLC separations being developed with these adsorbents.

The most important parameter in reversed-phase HPLC is the mobile phase. The type of mobile phase employed in the HPLC will have a significant effect on the retention of the analytes in the sample, and varying the composition of the mobile phase allows the chromatographer to adjust the retention times of target components in the mixture to desired values. This ability provides the HPLC method with flexibility. The mobile phase in reversed-phase chromatography has to be polar and it also has to provide reasonable competition for the adsorption sites for the analyte molecules. Solvents that are commonly employed as eluent components in reversed-phase HPLC are acetonitrile, dioxane, ethanol, methanol, isopropanol, tetrahydrofuran, and water. In reversed phase HPLC of high molecular weight biological compounds, the solvents acetonitrile, isopropanol or propanol are most frequently used. Popular additives to the mobile phase for the improvement of resolution include mixtures of phosphoric acid and amines and perfluorinated carboxylic acids, especially trifluoroacetic acid (TFA).

HPLC exploits the differences in affinity that a particular compound of interest has for the stationary phase and the mobile phase. This phenomenon can be utilized to separate compounds based on the differences in their physical properties. Thus, HPLC can be used to separate stereoisomers, diastereomers, enantiomers, mirror image stereoisomers, and impurities. Stereoisomers are those molecules which differ from each other only in the way their atoms are oriented in space. The particular arrangement of atoms that characterize a particular stereoisomer is known as its optical configuration, specified by known sequencing rules as, for example, either + or − (also D or L) and/or R or S. Stereoisomers are generally classified as two types, enantiomers or diastereomers. Enantiomers are stereoisomers which are mirror-images of each other. Enantiomers can be further classified as mirror-image stereoisomers that cannot be superimposed on each other and mirror-image stereoisomers that can be superimposed on each other. Mirror-image stereoisomers that can be superimposed on each other are known as meso compounds. Diastereomers are stereoisomers that are not mirror images of each other. Diastereomers have different physical properties such as melting points, boiling points, solubilities in a given solvent, densities, refractive indices, etc. Diastereomers can usually be readily separated from each other by conventional methods, such as fractional distillation, fractional crystallization, or chromatography, including HPLC.

Enantiomers, however, present special challenges because their physical properties are identical. They generally cannot be separated by conventional methods, especially if they are in the form of a racemic mixture. Thus, they cannot be separated by fractional distillation because their boiling points are identical and they cannot be separated by fractional crystallization because their solubilites are identical (unless the solvent is optically active). They also cannot be separated by conventional chromatography such as HPLC because (unless the adsorbent is optically active) they are held equally onto the adsorbent. HPLC methods employing chiral stationary phases are a very common approach to the separation of enantiomers. To be able to separate racemic mixtures of stereoisomers, the chiral phase has to form a diastereomeric complex with one of the isomers, or has to have some other type of stereospecific interaction. The exact mechanism of chiral recognition is not yet completely understood. In reversed-phase HPLC a common type of chiral bonded phase is chiral cavity phases.

The ability to be able to separate diastereomers and enantiomers by HPLC is a useful ability in evaluating the success of synthetic schemes. It is often desirable to separate stereoisomers as a means of evaluating the enantiomeric purity of production

SUMMARY OF THE INVENTION

The present invention is directed to a high performance liquid chromatography method to routinely and reproducibly detect and quantitate metal complexes. The method comprises loading a solution containing metal complexes onto a column, eluting the metal complex from the column with a mobile phase, the mobile phase comprising an excess of a salt of a coordinating anion in a solvent system, and detecting the metal complex with a detector. Eluting the complex from the column with the mobile phase generates a metal complex in which the coordinating anion (which is a competent ligand) out-competes all other potential ligands present for the available coordination sites on the metal. Thus, the role of this ligand is to, by the principles of mass action, occupy all the available ligand sites, creating one species. The metal complexes used in the method of the invention can be different metal complexes, or they can be stereoisomers of the same metal complexes. Thus, the HPLC method of the present invention is suitable for the separation of diastereomers of the same metal complexes.

Another embodiment of the present invention is directed to a chiral HPLC method to separate enantiomers of metal complexes. In this chiral HPLC method a chiral column is employed to achieve the separation of the enantiomers of metal complexes.

BRIEF DESCRIPTION OF THE DRAWINGS

FIG. 4 is HPLC chromatogram of M40403 using method 4.

FIG. 4a is a HPLC chromatogram of M40403 and related compounds using method 4.

FIG. 7 is a HPLC chromatogram of M40401 using method 2.

FIG. 8 is a HPLC chromatogram of M40401 using method 3.

FIGS. 12(A), 12(B), 12(C), 12(D), and 12(E) are HPLC Analyses of Diastereomers of M40403.

FIG. 13 is a Chiral HPLC profiles of the M40403 and M40419 bis(thiocyanato) enantiomers.

DETAILED DESCRIPTION OF THE INVENTION

Figure 1:
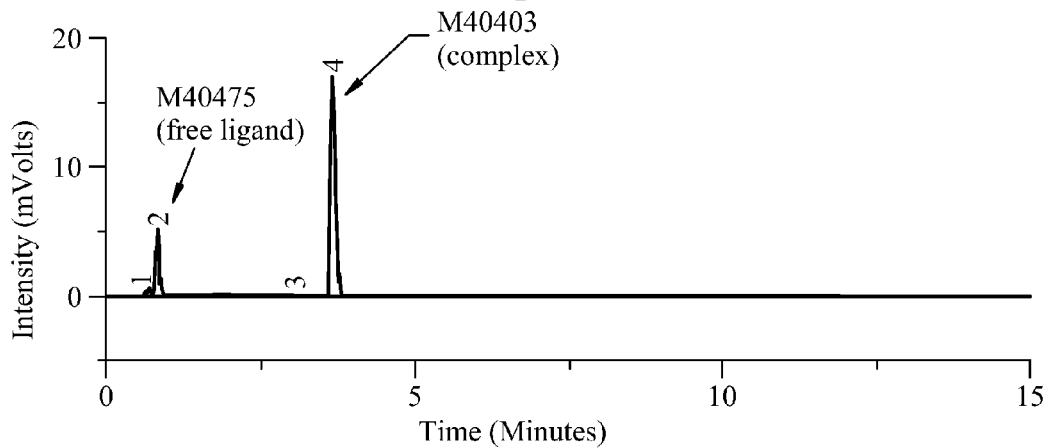
FIG. 1 is a HPLC chromatogram of M40403 using method 1.

The methods of the present invention provide an excess of a coordinating counterion in a mobile phase which will bind to the ligand sites on the metal of metal complexes. Solutions containing metal complexes are loaded onto a column and the metal complexes are eluted with the mobile phase. By inclusion of the excess of the counterion, the reaction is driven toward generating a single species during the elution with the mobile phase so that only one type of ligand, the counterion, is bound to the metal of the metal complex and all or substantially all the ligand binding sites of the metal are occupied by this one counterion. The formation of the single species is shown in Scheme 2. The formation of a single species of the metal complex(es) present allows the metal complexes to be reliably detected by a detector without interference from other species of complexes. The peaks on a chromatogram resulting from this detection are sharper and more resolved than those of a chromatogram resulting from a chromatography method in which a traditional mobile phase is employed, as demonstrated in Examples 1 (traditional mobile phase) and 2 (mobile phase containing excess of salt of a coordinating anion).

Scheme 2

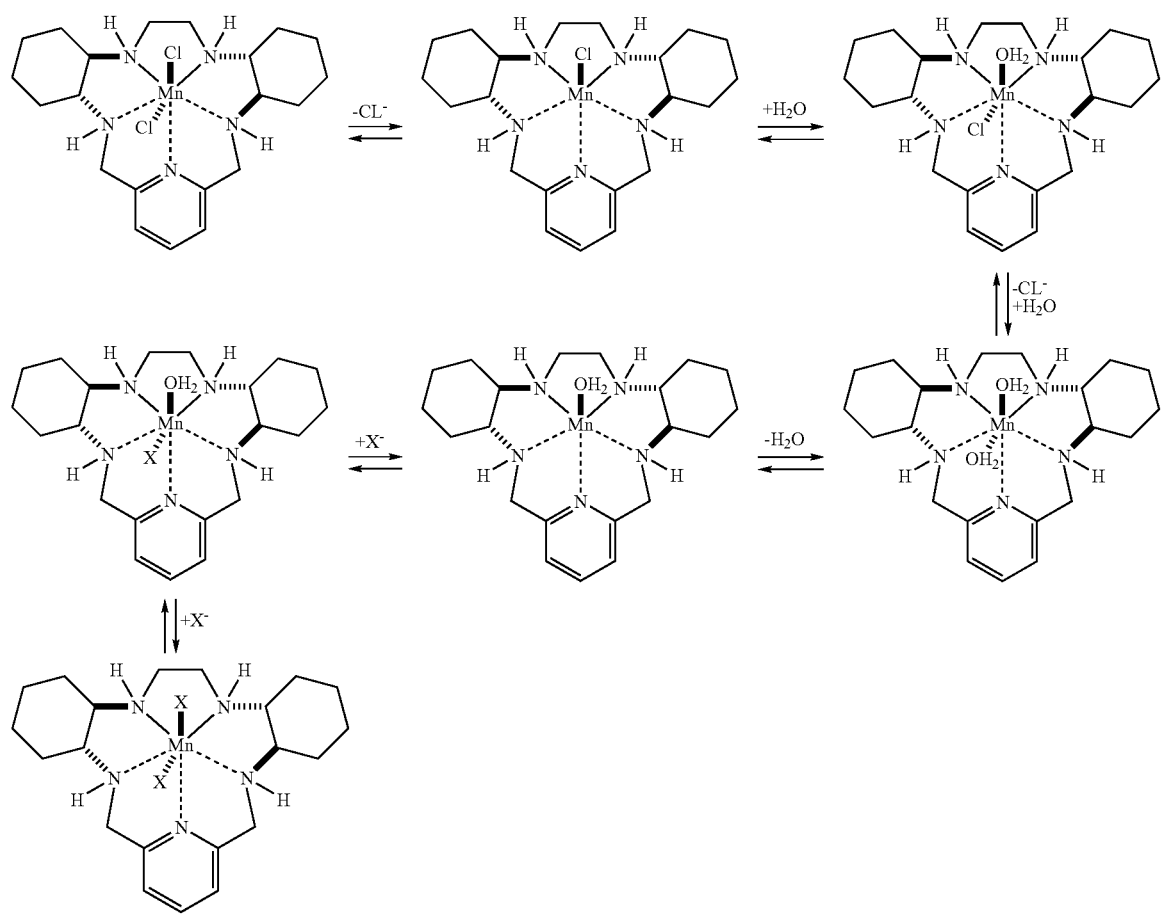

Any metal complex possessing a metal that is capable of coordinating a monodentate ligand can be used in the present invention. Examples of such metal complexes include, but are not limited to, complexes of the metals Mn and Fe. The metal complexes of the invention preferably have therapeutic and diagnostic utilities. These therapeutic and diagnostic utilities include, but are not limited to, use as superoxide dismutase mimetic compounds, MRI imaging enhancement agents, peroxynitrite decomposition catalysts, and catalase mimics. The preferred metal complexes for use in the invention are superoxide dismutase mimetic compounds. Examples of such superoxide dismutase mimetic compounds include, but are not limited to, the following complexes of the metals Mn and Fe. Iron based superoxide dismutase mimetics include, but are not limited to, $Fe^{III}$(salen) complexes, $Fe^{III}$(1,4,7,10,13-pentaazacyclopentadecane) derivatives and $Fe^{III}$(porphyrinato) complexes. Manganese based superoxide dismutase mimetic compounds include, but are not limited to, metal complexes containing manganese(II) or manganese(III). Examples of manganese based superoxide dismutase mimetic compounds include $Mn^{II}$(porphyrinato) complexes, $Mn^{III}$(salen) complexes, and $Mn^{II}$(1,4,7,10,13-pentaazacyclopentadecane) derivatives. $Mn^{II}$(1,4,7,10,13-pentaazacyclopentadecane) derivatives are more preferred for use in the invention. Examples of $Mn^{II}$(1,4,7,10,13-pentaazacyclopentadecane) derivatives preferred for use in the invention include, but are not limited to, M40403 and M40401, as shown in Scheme 3 below.

Furthermore, stereoisomers of all of the above metal complexes can be used in the process of the present invention. Diastereomers of the sane metal complexes can also be detected and separated by the method of the present invention. As it is often desirable to separate stereoisomers as a means of evaluating the chemical and optical purity of production samples, the metal complexes can also comprise products of a reaction stream. Enantiomers of any of the metal complexes referenced above can be used in the chiral HPLC method of the invention for the separation of enantiomers of a metal complex.

Scheme 3

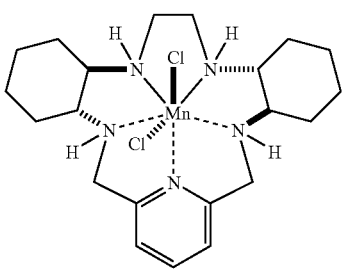

M40403

M40401

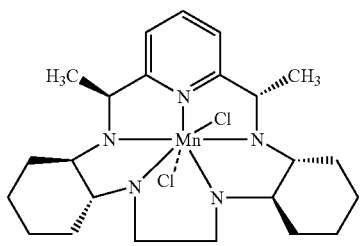

M40484

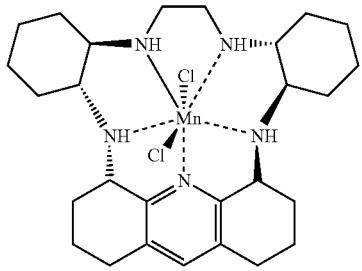

The ligand is a coordinating anion that binds to the metal cation of the metal complex. The coordinating anion can serve as an axial ligand for a superoxide dismutase mimetic compound. Examples of such anions include, but are not limited to, chloride anions, thiocyanate anions, stearate anions, acetate anions, trifluoroacetate anions, carboxylate anions, formate anions, or azide anions. Preferred anions include chloride anions, thiocyanate anions, and formate anions. More preferred anions are chloride anions. The more preferred anions in the chiral HPLC embodiment of the invention are thiocyanate anions. When present in an excess, the thiocyanate anions bind to the coordinating metal of the complexes preferentially to the chloride anions. An excess of thiocyanate anions will produce the bis(thiocyanato) complexes of M40403 and M40419 as shown in Scheme 4.

Scheme 4

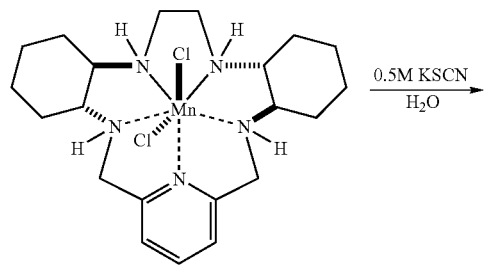

M40403

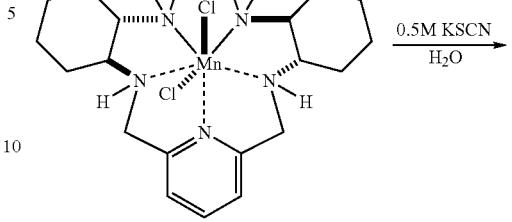

M40419

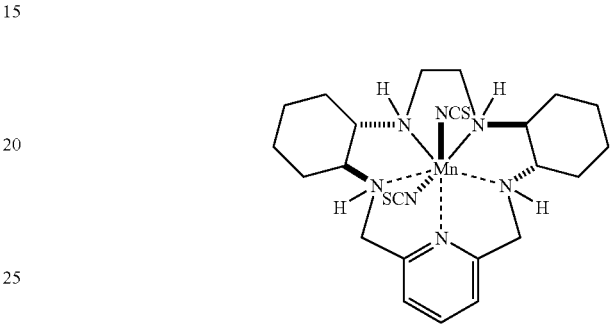

M40419-(SCN)$_2$

An example of the use of the acetate anion as the coordinating anion with M40403 is shown in Scheme 5 below. Scheme 6 illustrates the use of the formate anion as the coordinating anion with M40403.

Scheme 5

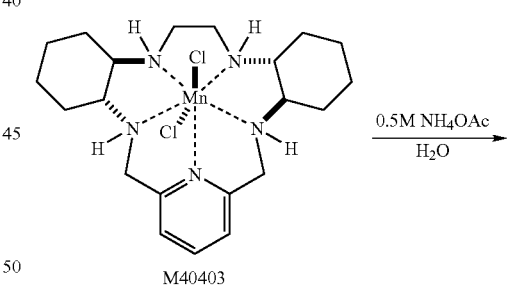

M40403

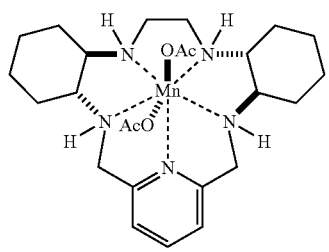

M40403-(OAc)$_2$

Scheme 6

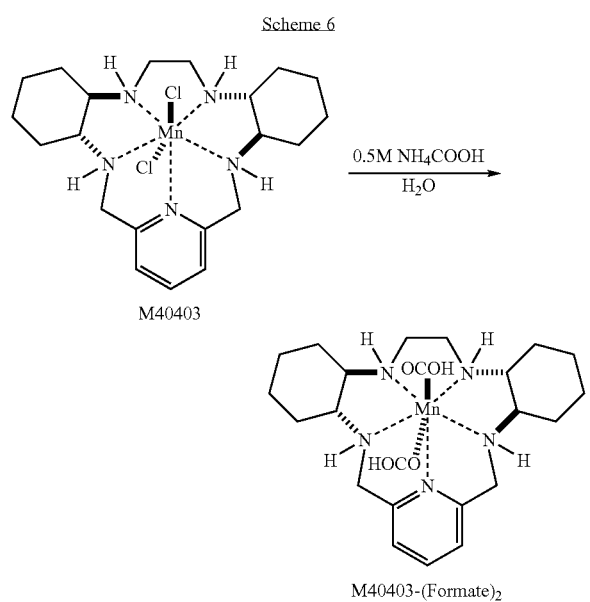

The coordinating anion is supplied by a salt of the coordinating anion. Salts of the chloride anion include, but are not limited to, sodium chloride, lithium chloride, potassium chloride, ammonium chloride, or tetraalkylammonium chloride. Preferred salts of the chloride anion include sodium chloride, lithium chloride and tetrabutylammonium chloride. Salts of the thiocyanate anion include, but are not limited to, sodium thiocyanate, potassium thiocyanate, ammonium thiocyanate, or lithium thiocyanate. Preferred salts of the thiocyanate anion include sodium thiocyanate and potassium thiocyanate. Salts of the acetate anion include, but are not limited to, potassium acetate, sodium acetate, ammonium acetate, ammonium trifluoroacetate and lithium acetate. Preferred salts of the acetate anion include ammonium acetate. Salts of the formate anion include, but are not limited to, potassium formate, sodium formate, ammonium formate and lithium formate. Preferred salts of the formate anion include ammonium formate. Salts of the cyanate anion include but are not limited to, sodium cyanate, potassium cyanate, or ammonium cyanate. Salts of the carboxylate anion include, but are not limited to, potassium carboxylate, ammonium carboxylate and sodium carboxylate. Salts of the stearate anion include, but are not limited to, lithium stearate and sodium stearate. Salts of the azide anion include, but are not limited to, sodium azide, potassium azide, and lithium azide. The salt added to the mobile phase can also be a mixture of any of these salts. Examples include a mixture of tetrabutylammonium chloride and lithium chloride.

The solvent system can comprise any solvent employed in HPLC procedures. The solvent system can comprise a single solvent or a mixture of solvents as long as salts of the coordinating anion are soluble in the solvent system. Examples of suitable solvents include, but are not limited to, acetonitrile, dioxane, ethanol, methanol, isopropanol, tetrahydrofuran, and water. Preferred solvents for all embodiments of the invention include acetonitrile, isopropanol, propanol, water, and methanol. More preferred solvents are acetonitrile, water and methanol. Suitable mixtures of solvents can be, for example, mixtures of acetonitrile and water or mixtures of methanol and water. The more preferred solvent for the chiral HPLC embodiment of the invention is methanol.

The solvent system containing the excess of salt and optionally a base or acid for pH adjustment comprises the mobile phase. The composition of the mobile phase is important to the success of the method of the present invention. The amount of the salt of the coordinating anion should be in sufficient excess for the coordinating anion to saturate substantially all, and preferably, all of the exchangeable ligand binding sites on the metal of the metal complexes, driving the formation of a single species during elution with the mobile phase. The single species is substantially formed during elution with the mobile phase. A substantial formation of a single species, a complex in which the coordinating anion of the salt comprises the ligands, is that amount of single species that produces enhanced resolution and improved peak shape in a chromatogram compared to a chromatogram from an HPLC in which either no salt or an insufficient amount of salt has been used in the mobile phase. This enhanced resolution and improved peak shape is illustrated in the FIG. 2 chromatogram of Example 2 and should occur without the metal complex dissociating. An example of a chromatogram from an HPLC in which either no salt or an insufficient amount of salt has been used in the mobile phase is FIG. 1 in Example 1.

The salt of the coordinating anion is present in excess in the mobile phase. The concentration of salt in the mobile phase can vary considerably, depending on the composition of the mobile phase and the particular type of salt employed. Upper limits on the concentration of salt in the mobile phase are set by the solubility of the salt in the mobile phase. Lower limits on the concentration of salt in the mobile phase are set by the concentration of salt that provides an amount of a coordinating anion sufficient to cause the formation of a metal complex possessing substantially only the coordinating anion as ligands. The lower limit of the concentration of salt in the mobile phase is at least greater than a stoichiometrical amount. Preferably, the salt is present in the mobile phase at a concentration that maximizes the formation of a single species. Generally, however, the concentration of the salt in the mobile phase varies from between about 0.004 M to about 6 M. Preferably, the concentration of the salt in the mobile phase varies from between about 0.1 M to about 1 M. More preferably, the concentration of the salt in the mobile phase varies from between about 0.15 M to about 0.6 M.

These ranges will differ depending upon the type of salt employed in the mobile phase. For example, the concentration of sodium chloride in the mobile phase ranges from between about 0.1 M to about 1 M NaCl. Preferably, the concentration of sodium chloride in the mobile phase ranges from between about 0.3 M to about 0.7 M. More preferably, the concentration of sodium chloride in the mobile phase ranges from between about 0.4 to about 0.6 M. The concentration of lithium chloride in the mobile phase ranges from between about 0.1 M to about 1 M NaCl. Preferably, the concentration of lithium chloride in the mobile phase ranges from between about 0.3 M to about 0.7 M. More preferably, the concentration of lithium chloride in the mobile phase ranges from between about 0.4 M to about 0.6 M. The concentration of tetrabutylammonium chloride in the mobile phase ranges from between about 0.005 M to about 0.15 M. Preferably, the concentration of tetrabutylammonium chloride in the mobile phase ranges from between about 0.01 M to about 0.13 M. More preferably, the concentration of tetrabutylammonium chloride in the mobile phase ranges from between about 0.05 M to about 0.125 M.

The mobile phase should have a pH that is appropriate to the metal complexes employed in the method and the column employed in the method. A pH that is appropriate to the metal complexes employed in the method is a pH at which the metal complex is stable, i.e. that does not cause the metal complex to dissociate. A pH that is appropriate for the column employed in the method of the invention is a pH at which the column is stable and functions properly. The pH of the mobile phase can be adjusted by the addition of a base or an acid. The need for an adjustment of the pH will depend on many factors, including the particular metal complexes used, the type of column employed and the composition of the mobile phase. Thus, the pH of the mobile phase could be anywhere from 2-14.

However, for the preferred metal complexes of the invention the pH is preferably between 6-8. A pH between 6-8 minimizes complex dissociation. Proton assisted complex dissociation is a phenomenon whereby the metal complex becomes protonated and due to this protonation more readily dissociates. The complex experiences more protonation at lower pH values. More preferably, the pH of the mobile phase is between about 6.0 to about 7.5. Even more preferably, the pH of the mobile phase is between about 6.4 to about 7.2. The pH of the mobile phase can be adjusted to these preferred values using any appropriate base. Examples of suitable bases include, but are not limited to, sodium hydroxide, lithium hydroxide, potassium hydroxide, and ammonium hydroxide. Preferably, the cation of the base corresponds to the cation of the salt in the mobile phase. For example, a preferred base for use in a solvent system containing sodium chloride would be sodium hydroxide. Similarly, a preferred base for use in a mobile phase containing tetrabutylammonium chloride would be ammonium hydroxide. The amount of base in the mobile phase will be that amount needed to adjust the mobile phase to the appropriate pH.

Thus, an example of a suitable mobile phase is acetonitrile in water containing between about 0.1 M to about 0.7 M of a salt at a pH of between about 6 to about 8. Another suitable mobile phase is 1-5% methanol in water containing between about 0.15 M to about 0.6 M of salt at a pH of between about 6 to about 8. A preferred mobile phase would be acetonitrile containing between about 0.3 M to about 0.7 M of sodium chloride at a pH of between about 6.0 to about 7.5. Another preferred mobile phase would be 5-15% acetonitrile in water containing between about 0.01 M to about 0.13 M of tetrabutylammonium chloride at a pH of between about 6.0 to about 7.5. Still another preferred mobile phase would be 5-15% acetonitrile in water containing a mixture of between about 0.01 M to about 0.13 M of tetrabutylammonium chloride and between about 0.3 M to about 0.7 M lithium chloride at a pH of between about 6.0 to about 7.5.

A more preferred mobile phase would be 5-10% acetonitrile in water containing between about 0.4 M to about 0.6 M of sodium chloride at a pH of between about 6.4 to about 7.2. Another more preferred mobile phase would be 5-10% acetonitrile in water containing between about 0.05 M to about 0.125 M of tetrabutylammonium chloride at a pH of between about 6.4 to about 7.2. Still another preferred mobile phase would be 5-10% acetonitrile in water containing a mixture of between about 0.05 M to about 0.125 M of tetrabutylammonium chloride and between about 0.4 M to about 0.6 M lithium chloride at a pH of between about 6.4 to about 7.2.

For the chiral HPLC embodiment of the invention a preferred mobile phase would include 1-5% methanol in water containing between about 0.1 M to about 2.5 M of ammonium thiocyanate. Another preferred mobile phase would be 1-5% methanol in water containing between about 0.05 M to about 0.3 M of tetrabutylammonium chloride. A more preferred mobile phase for the chiral HPLC embodiment would be 1-5% methanol in water containing between about 0.2 M to about 0.3 M of ammonium thiocyanate. Another more preferred mobile phase would be 1-5% methanol in water containing between about 0.05 M to about 0.15 M of tetrabutylammonium chloride.

In the first step of the analytical method a solution containing the metal complex is loaded onto the column. The loading can be accomplished by injection or another suitable means of placing the solution containing the metal complex onto the column. Preferably, the solution containing the metal complex is loaded on the column by injection through an injector. The process of injection can be manual or it may be automated. The preparation of the metal complex for injection could occur in several ways. Preferably, the metal complex is directly dissolved in the mobile phase. However, depending on the solubility of the metal complex, the metal complex can also be dissolved in a solvent and then the mobile phase could be added to it. Another way of accomplishing the combining step is to dissolve the metal complex in a solvent with a salt of the same coordinating anion that is present in the mobile phase and then dilute with a mobile phase. Suitable solvents in which the metal complexes could be dissolved include organic solvents such as methanol, ethanol, and propanol. The solvent in which the metal complexes can be dissolved does not have to be the same solvent or solvents that comprise the solvent system in the mobile phase. However, it is preferred that the solvent in which the metal complexes are dissolved be the same solvent or solvents that comprise the solvent system in the mobile phase. Thus, the solution containing the metal complexes can be the mobile phase, a suitable solvent that dissolves the metal complexes, or a suitable solvent that dissolves the metal complexes that has been further diluted with mobile phase.

An additional optional step in the method of both the chiral HPLC and achiral HPLC embodiment of the invention is to form a metal complex containing only one type of coordinating anion as ligands before combining the metal complex with the mobile phase. The single species is formed by combining an excess of the salt of a coordinating anion with a metal complex in an aqueous solution to generate a single species of the metal complex. Following the addition of the excess of the salt of the coordinating anion to the aqueous solution, the solution is agitated to form a homogenous solution. The agitation ensures that all of the ligand binding sites of the metal of the metal complex are occupied by the coordinating anions to form a single species. The agitation continues for a period of time ranging from a few minutes to several hours until a homogeneous solution is achieved. For example, a bis(thiocyanato) complex could be formed from the metal complex by combining an excess of potassium thiocyanate with the metal complex in water. The resulting solution or suspension is extracted with methylene chloride to provide the thiocyanate complex of the metal complex. The metal complex can then be combined with a thiocyanate salt in the solvent system as a bis(thiocyanato) complex.

Suitable stationary phases for use in the method of the invention include the columns commonly used in HPLC methods. Any HPLC column can be utilized provided that it can provide successful separation of metal complexes. Columns typically range from 2-5 mm in diameter with particles of size ranging from 3-10 mm. Examples of suitable columns include C1 modified columns, C3 modified columns, C4 modified columns, octyl (C8) modified columns, octadecyl (C18) modified columns, C18 polymer column, phenyl columns, and amino-cyano columns. Preferred types of columns include octadecyl modified columns, phenyl columns, and amino-cyano columns. More preferred types of columns include octadecyl modified columns. Examples of these more preferred octadecyl modified columns include the YMC ODS-AQ S5 Column® available from Waters Corporation, Vydac Column® available from Vydac, and the Symmetry Shield RP$_{18}$ Column® available from Waters Corporation.

In the chiral HPLC embodiment of the invention a chiral stationary phase should be employed. Any type of chiral column utilized in HPLC can be employed in the invention provided it successfully separates enantiomers of metal complexes. Chiral columns employed with high performance liquid chromatography are preferred for use in the invention. Thus, preferred columns typically range from 2-5 mm in diameter with particles of size ranging from 3-10 mm. Examples of suitable chiral stationary phases include cellulose based columns and Pirkie columns. A preferred chiral column is the Chiralcel-OD-RH Column® available from Chiral Technology.

Eluting the complex from the column with the mobile phase generates a metal complex in which the coordinating anion (which is a competent ligand) out-competes all other potential ligands present for the available coordination sites on the metal. The composition of the mobile phase can be varied during the elution to meet the objectives of a particular chromatography experiment. Thus, isocratic or gradient elution can be employed with the method of the invention. The mobile phase is passed through the column at a determined flow rate. Evaluating these factors and arriving at an appropriate flow rate for the objectives of the HPLC method can be accomplished by one of ordinary skill in the art. The rate at which the compound will elute from the column will depend on the metal complex's affinity for the mobile phase relative to its affinity for the column. This will in turn depend on the type of column employed in the method of the invention, the composition of the mobile phase, and the flow rate of the mobile phase through the column. The appropriate flow rate for a column will depend on the nature of the column, including the column's length and tolerance of pressure, the particular metal complexes being eluted from the column, and the composition of the mobile phase. Generally, the flow rate can range from about 0.1 to about 10.0 ml/min. A preferred flow rate would be between about 0.5 to about 3 ml/min. For example, for a 25 cm SymmetryShield RP$_{18}$ Column® a typical flow rate will range from about 0.5 to about 2 ml/min. A preferred flow rate would be between about 0.9 to about 1.2 ml/min. The typical flow rate for a YMC ODS-AQ S5 Column® that is 5 cm in length ranges from 0.5 to 4 ml/min. The preferred flow rate for a YMC ODS-AQ S5 Column® ranges from 2 to 3 ml/min.

After the metal complex is eluted from the column the compound is detected by a detector. The detecting can be performed by any detector appropriate to meet the objectives of the HPLC procedure. The detecting may be performed by an "on-line" detector or an "off-line" detector. An "on-line" detector, as utilized herein, is a detector that is directly coupled to the column and detects the metal complex as it elutes from the column. An "off-line" detector, as utilized herein, is a detector that is not directly coupled to the column, but detects the metal complex after it has been collected and manually transferred to the detector. Thus, the detecting may be manual or automated. On-line detectors are preferred for use in the invention. Examples of suitable detectors for the metal complexes include, but are not limited to, refractive index detectors, radiochemical detectors, electrochemical detectors, and mass spectroscopy detectors. Ultraviolet/visible absorption detectors are a preferred type of detector for use in the chromatographic method of the invention. Ultraviolet/visible absorption detectors include fixed wavelength detectors, variable wavelength detectors, and diode array detectors. Fixed wavelength detectors measure at one wavelength, typically 254 or 264 nm. Variable wavelength detectors measure at one wavelength at a time, while diode array detectors measure a spectrum of wavelengths simultaneously. Fixed wavelength UV detectors are preferred for use in the invention.

High performance liquid chromatography procedures are widely used analytical methods that are very familiar to those of ordinary skill in the art. Selecting the appropriate equipment and parameters for a particular HPLC procedure and making the appropriate variations in the procedure to meet the objective of a particular experiment are readily accomplished by one of ordinary skill in the art. The methods of each embodiment of the invention can be used with any HPLC machine, provided that a chiral column is employed in the chiral HPLC embodiment of the invention. The method of the present invention can be used with either normal phase or reverse phase HPLC depending upon the selection of solvents and columns. Furthermore, the methods of the present invention are not limited to any particular scale, however, it is preferred that the method be operated using metal complex sample sizes similar to those employed in high performance liquid chromatography.

Thus, in each embodiment of the present invention there is provided a HPLC method in which a single species of the metal complex(es) present can be reliably generated so that detection and quantification of the metal complexes can proceed without interference from other complexes. The following examples are intended to illustrate but not to limit the invention.

EXAMPLES

Experimental For Examples 1-8

Chemicals, Solvents and Materials

All solvents used in the study were HPLC grade or equivalent. All chemicals were ACS reagent grade or equivalent.

HPLC System and Data Analysis

The HPLC chromatography was performed using a Gilson system (Model 306 pump, Model 155 UV-V detector, Model 215 liquid handler, Unipoint Software, Win98), a Varian system (Model 310 pump, Model 340 UV-V detector, Model 410 autosampler Star Workstation, Win98) or SSI system (Acuflow Series IV pump, Acutect 500 UV-V detector, Alcott Model 718 autosampler, HP Model 3395 integrator).

Example 1

HPLC Analysis of M40403 using Method 1

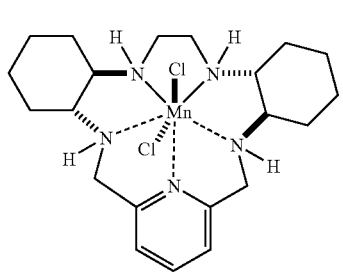

Method 1: Analytical Column: Waters YMC ODS-AQ S5 120 Å (4.6×50 mm);

System A: 0.1% trifluoroacetic acid in $H_2O$; System B: 0.08% trifluoroacetic acid in acetonitrile; Gradient: 10-50% system B over 10 min; Flow rate: 3 ml/min; Detector wavelength: 265. Injected 20 μl of stock solution of M40403 prepared by dissolving 1 mg in 1 ml of water and diluting with 1 ml of system A. The HPLC chromatogram of M40403 using method 1 is shown in FIG. 1.

Example 2

HPLC Analysis of M40403 Using Method 2

Figure 2:
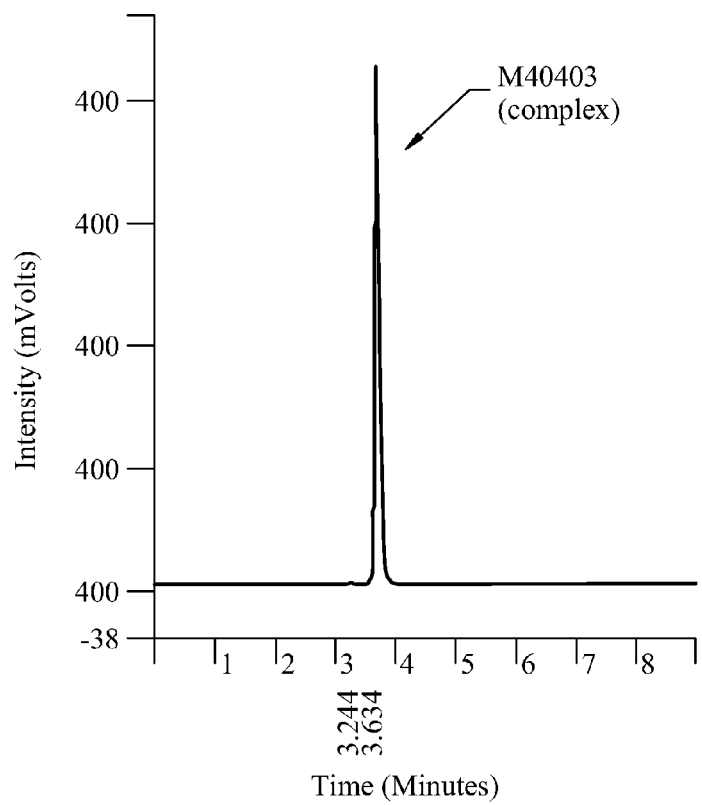
FIG. 2 is a HPLC chromatogram of M40403 using method 2.

Method 2: Analytical Column: Waters YMC 9DS-AQ S5 120 Å (4.6×50 MM); System A: 0.5 N aqueous NaCl; System B: 1:4 water/$CH_3CN$; Gradient: 10-50% system B over 9 min; Flow rate: 3 mL/min; Detector wavelength: 265 nm. Injected 20 μl of stock solution of M40403 prepared by dissolving 1 mg in 1 ml of system A. The HPLC chromatogram of M40403 using method 2 is shown in FIG. 2.

Example 3

HPLC Analysis of M40403 Using Method 3

Figure 3:
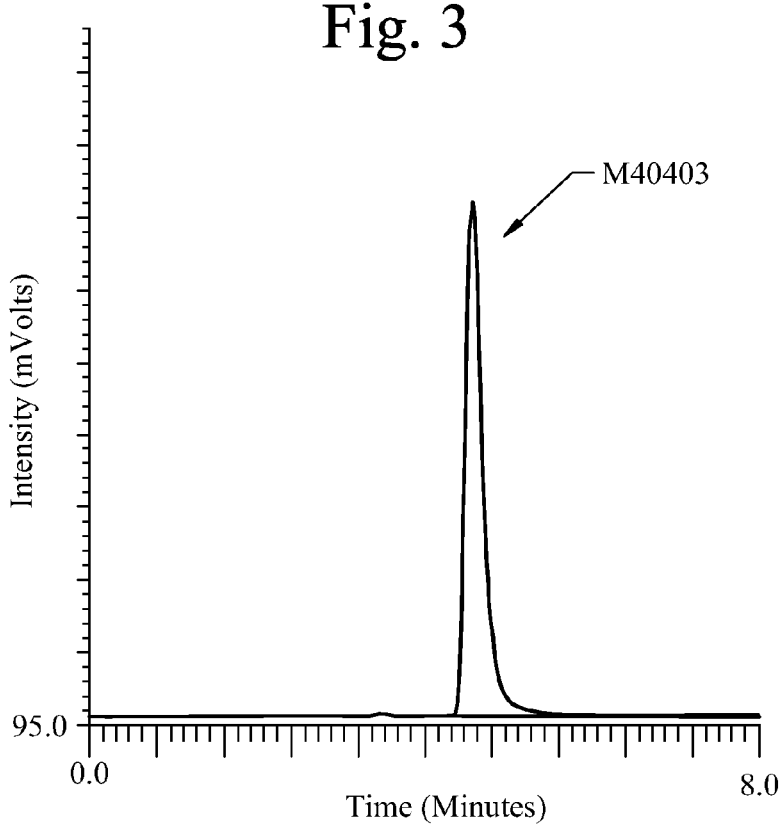
FIG. 3 is a HPLC chromatogram of M40403 using method 3.

Method 3: Analytical Column: Waters Symmetry Shield RP18, 5 μm, 250×4.6 mm;
Mobile Phase: Acetonitrile: 0.125 M Tetrabutylammonium Chloride in water (pH 6.5), 5%:95% $H_2O$(v/v); Flow rate: 1 ml/min; Detection wavelength: 265 nm. Injected 20 μl of stock solution of M40403 prepared by dissolving 1 mg in 1 ml of mobile phase. The HPLC chromatogram of M40403 using method 3 is shown in FIG. 3.

Figure 3A:
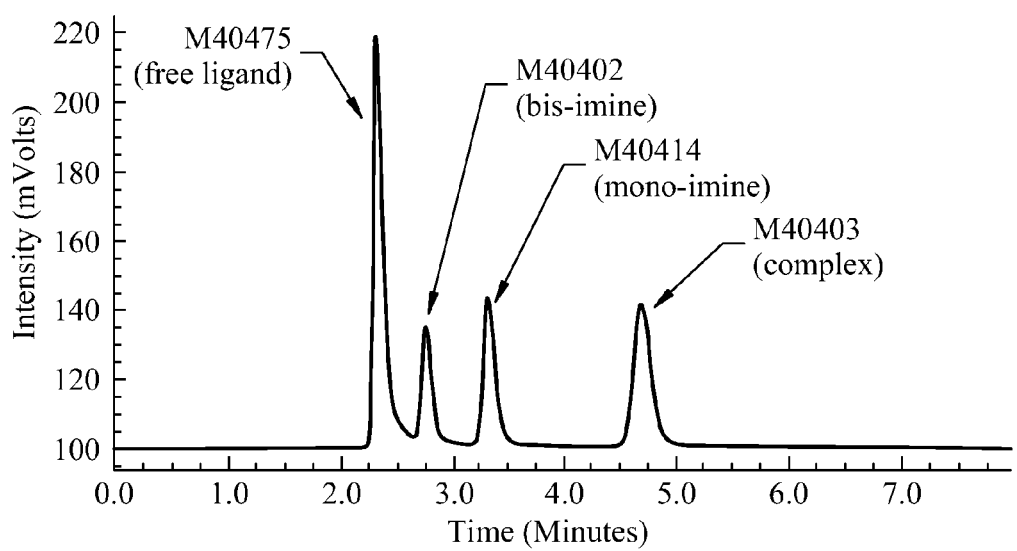
FIG. 3a is a HPLC chromatogram of M40403 and related compounds using method 3.

The HPLC chromatogram of M40403 and related compounds using method 3 is shown in FIG. 3*a*. Method 3 allows a separation of M40402 (bisimine of M40403), M40414 (monoimine of M40403) and M40475 (free ligand of M40403) (see chromatogram in FIG. 3*a*).

Example 4

HPLC Analysis of M40403 Using Method 4

Method 4: Analytical Column: Waters Symmetry Shield RP18, 5 μm, 250×4.6 mm;
Mobile Phase Acetonitrile: 0.125 M Tetrabutylammonium Chloride and 0.5 M LiCl in water (pH 6.5), 5%:95% $H_2O$ (v/v); Flow rate: 1 mL/min; Detection wavelength: 265 nm. Injected 20 μl of stock solution of M40403 prepared by dissolving 1 mg in 1 ml of system A. The HPLC chromatogram of M40403 using method 4 is shown in FIG. 4.

The HPLC chromatogram of M40403 and related compounds using method 4 is shown in FIG. 4*a*. Method 4 allows a separation of M40402 (bisimine of M40403), M40414 (monoimine of M40403) and M40475 (free ligand of M40403) and all diastereomers of M40403 (see chromatogram in FIG. 4*a*).

Example 5

HPLC Analysis of M40401 Using Method 1

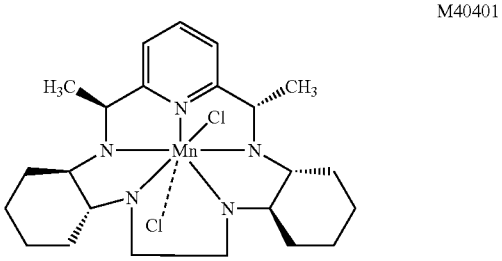

M40401

Figure 5:
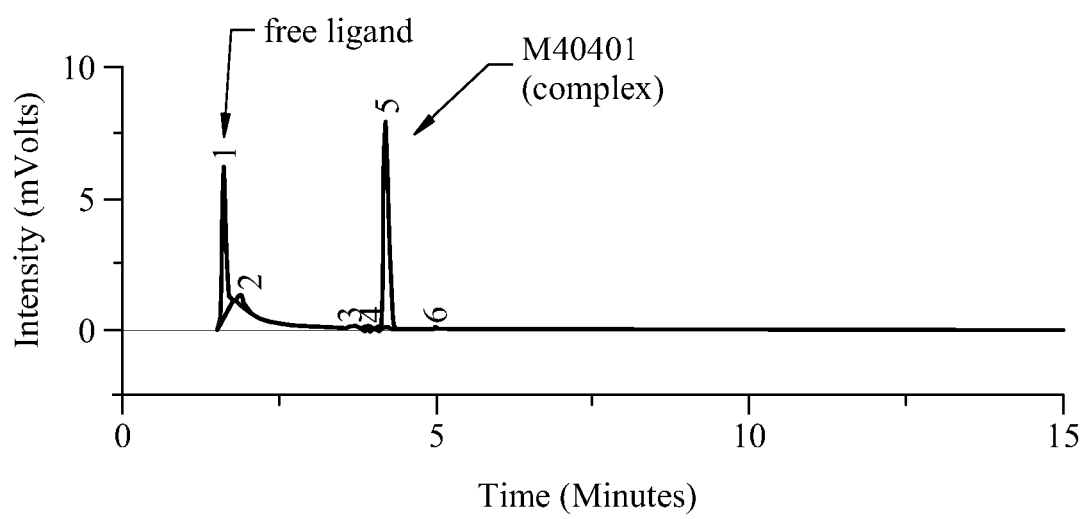
FIG. 5 is a HPLC chromatogram of M40401 using method 1.

Method 1: Analytical Column: Waters YMC ODS-AQ S5 120 Å (4.6×50 mm);
System A: 0.1% trifluoroacetic acid in $H_2O$; System B: 0.08% trifluoroacetic acid in acetonitrile; Gradient: 10-50% system B over 10 min; Flow rate: 3 ml/min; Detector wavelength: 265. Injected 20 μl of stock solution of M40401 prepared by dissolving 1 mg in 1 ml of water and diluting with 1 ml of system A. The HPLC chromatogram of M40401 using method 1 is shown in FIG. 5.

Example 6

HPLC with Various NaCl Concentrations

Figure 6:
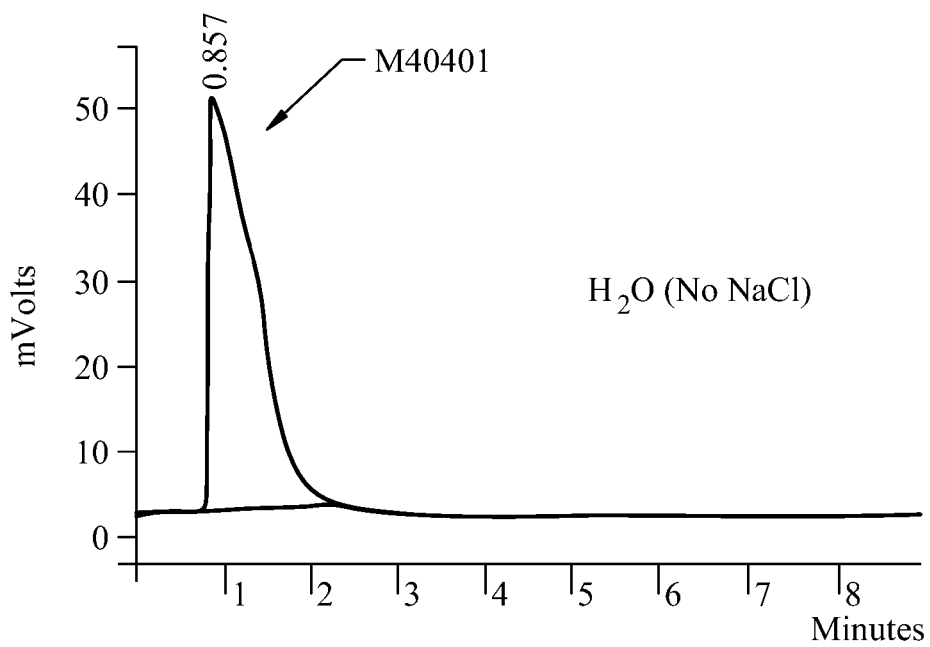
FIGS. 6(A), 6(B), and 6(C) are HPLC chromatograms of M40401 with various NaCl concentrations.

An HPLC was taken of M40401 with various concentrations of NaCl.
Analytical Column: Waters YMC 9DS-AQ S5 120 Å (4.6×50 mm);
System A: (A) $H_2O$ (no NaCl); (B) 0.01 M NaCl in water; (C) 0.5 M NaCl in water;
System B: acetonitrile; Gradient: 0-100% system B over 10 min; Flow: 3 ml/min;
Detector wavelength: 265 nm. Injected 20 μl of stock solution of M40401 prepared by dissolving 1 mg in 1 ml of system A. The HPLC chromatogram of M40401 using various NaCl concentrations is shown in FIG. 6.

Example 7

HPLC Analysis of M40401 Using Method 2

Method 2: Analytical Column: Waters YMC ODS-AQ S5 120 Å (4.6×50 MM);
System A: 0.5 N aqueous NaCl; System B: 1:4 water/$CH_3CN$; Gradient 1: 10-50% system B over 9 min; Flow rate: 3 mL/min; Detector wavelength: 265 nm. Injected 20 μl of stock solution of M40403 prepared by dissolving 1 mg in 1 ml of system A.

The HPLC chromatogram of M40401 using method 2 is shown in FIG. 7. Method 2 allows a separation of M40472

(bisimine of M40401), M40473 (monoimine of M40401), free ligand of M40403 and two isomers of M40401 (M40406, M40404).

Example 8

HPLC Analysis of M40401 Using Method 3

Method 3: Analytical Column: Waters Symmetry Shield RP18, 5 m, 250×4.6 mm;
Mobile Phase: Acetonitrile: 0.125 M Tetrabutylammonium Chloride in $H_2O$ (pH 6.5), 5:95% $H_2O$ (v/v); Flow rate: 1 mL/min; Detection wavelength: 265 nm.

The HPLC chromatogram of M40401 using method 3 is shown in FIG. 8.
Method 3 allows a separation of M40472 (bisimine of M40401), M40473 (monoimine of M40401), free ligand of M40403 and two isomers of M40401 (M40406, M40404).

Example 9

HPLC Analysis of M40401 Using Method 4

Figure 9:
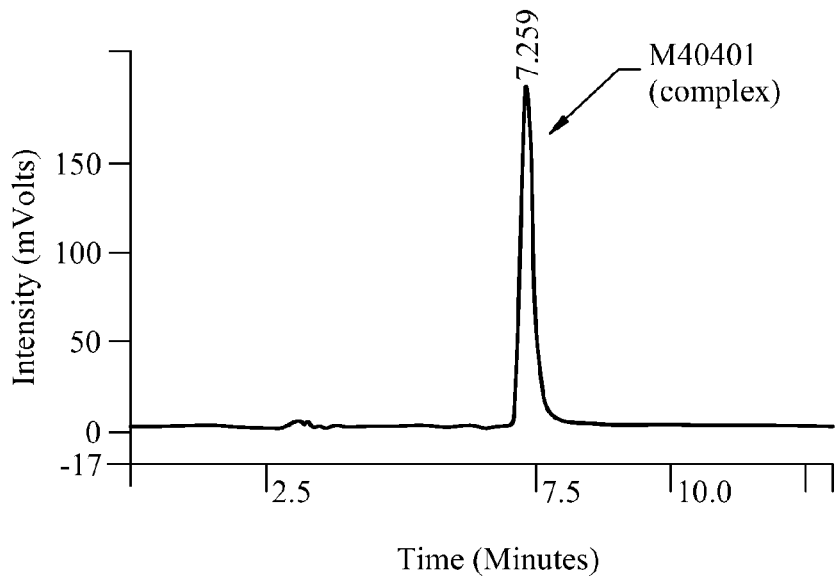
FIG. 9 is a HPLC chromatogram of M40401 using method 4.

Method 4: Analytical Column: Waters Symmetry Shield RP18, 5 µm, 250×4.6 mm;
Mobile Phase: Acetonitrile: 0.125 M Tetrabutylammonium Chloride and 0.5 M LiCl in water (pH 6.5), 5:95% $H_2O$ (v/v); Flow rate: 1 mL/min, Detection wavelength: 265 nm; Injected 20 µl of stock solution of M40401 prepared by dissolving 1 mg in 1 ml of a mobile phase. The HPLC chromatogram of M40401 using method 4 is shown in FIG. 9.

Figure 9A:
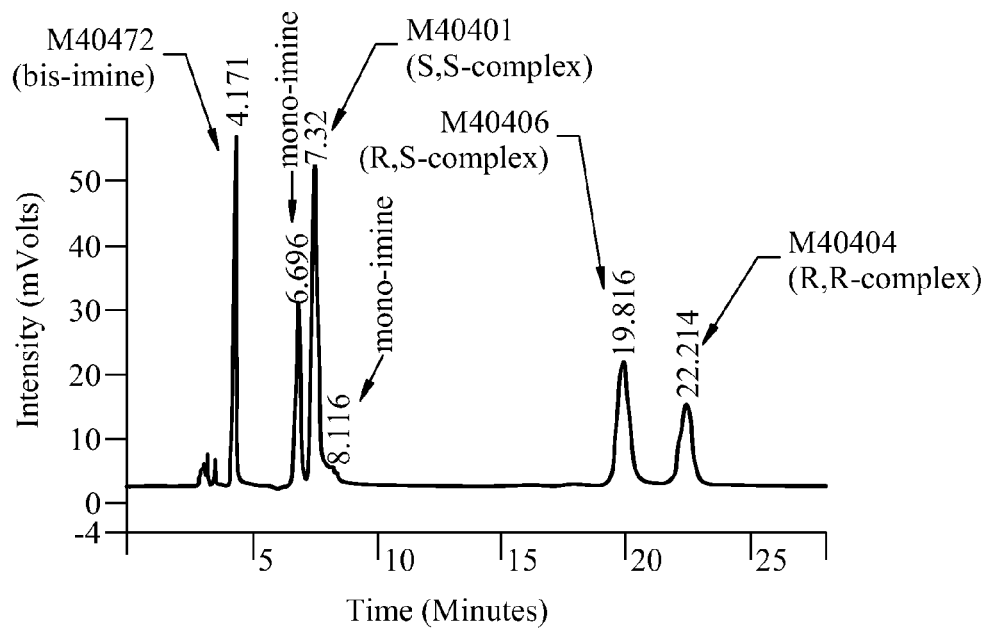
FIG. 9a is a HPLC chromatogram of a mixture of M40401 and related compounds.

The HPLC chromatogram of M40401 and related compounds using method 4 is shown in FIG. 9a. Method 4 allows a separation of M40472 (bisimine of M40401), M40473 (monoimine of M40401), free ligand of M40403 and two isomers of M40401 (M40406, M40404).

Example 10

HPLC of M40403-(HCOO⁻)₂ Using Formate Anion

An HPLC of M40403 employing the formate anion was taken.
Analytical Column: Waters YMC 9DS-AQ S5 120 Å (4.6×50 mm);
System A: 0.025 M ammonium formate in water; System B: 1:4=0.125 M ammonium formate in water/acetonitrile; Gradient: 0-100% system B over 10 min;
Flow: 3 ml/min;
Detector wavelength: 265 nm. Injected 20 µl of stock solution of M40403-(Formate)₂ prepared by dissolving 1 mg in 1 ml of system A.

Figure 10:
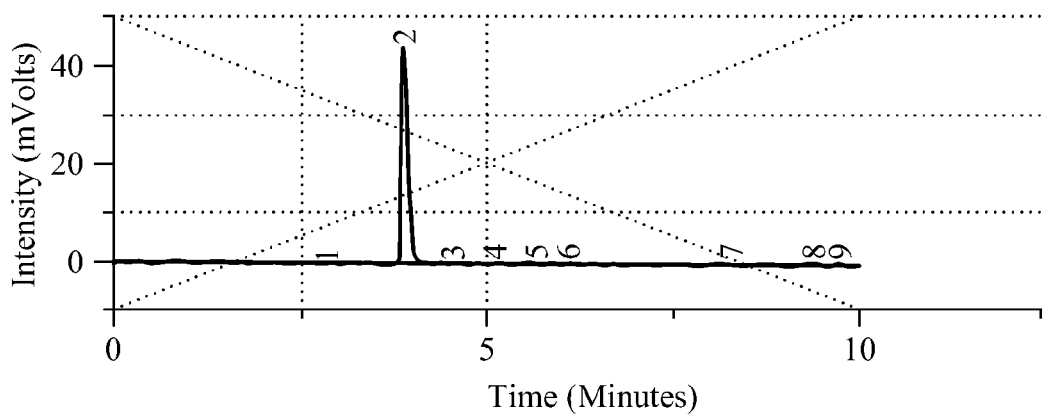
FIG. 10 is a HPLC chromatogram of M40403-$(HCOO^-)_2$ using formate anion.

The HPLC chromatogram of M40403-(HCOO⁻)₂ is shown in FIG. 10.

Example 11

HPLC of M40403-(OAc)₂ Using Acetate Anion

An HPLC of M40403 employing the acetate anion was taken.
Analytical Column: Waters YMC 9DS-AQ S5 120 Å (4.6×50 mm);
System A: 0.025 M ammonium acetate in water; System B: 1:4=0.125 M ammonium acetate in water/acetonitrile; Gradient: 0-100% system B over 10 min; Flow: 3 ml/min;
Detector wavelength: 265 nm. Injected 20 µl of stock solution of M40403-(OAc)₂ prepared by dissolving 1 mg in 1 ml of system A.

Figure 11:
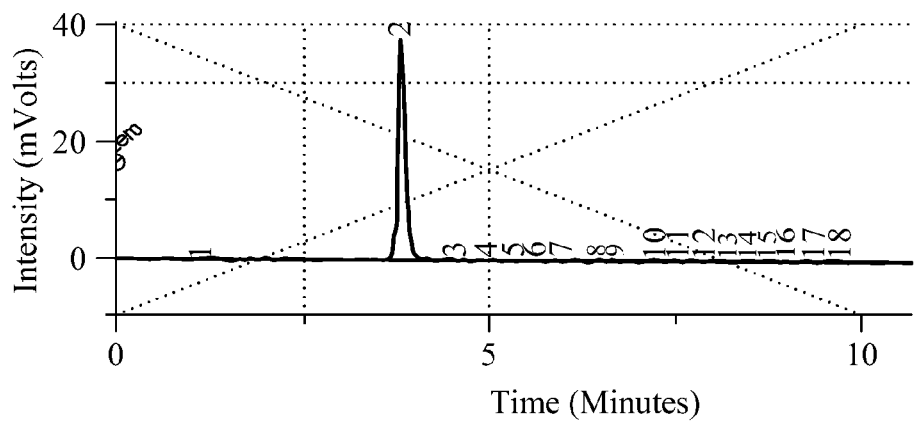
FIG. 11 is a HPLC chromatogram of M40403-$(CH_3COO^-)_2$ using acetate anion.

The HPLC chromatogram of M40403-(OAc)₂ is shown in FIG. 11.

Example 12

An HPLC method to separate the diastereomers of superoxide dismutase mimetic compound M40403. Four stereoisomer mixtures were prepared (Part A) as shown in Schemes 5-9 and then separated (Part B) via reversed-phase high performance liquid chromatography.

Part A

Synthesis of Stereoisomers Of M40403

M40403 is synthesized from its single-isomer, tetra-amine precursor M40400 in the reaction shown in Scheme 7.

Scheme 7

The various stereoisomers of M40403 are synthesized from the various isomers of 1,2-diaminocyclohexane which provides the chiral carbon centers in M40403. The 1,2-diaminocyclohexane isomers used to prepare the (R,R+R,S) M40403 stereoisomer mixture of Set 1 are shown in Scheme 6. Similarly, the 1,2-diaminocyclohexane isomers used to prepare the (R,R+S,S) M40403 stereoisomer mixture of Set 2 are shown in Scheme 7. The 1,2-diaminocyclohexane isomers used to prepare the (R,S+R,S) M40403 stereoisomer mixture of Set 3 are shown in Scheme 8. The 1,2-diaminocyclohexane isomers used to prepare the (S,S+R,S) M40403 stereoisomer mixture of Set 4 are shown in Scheme 9. As shown in Schemes 6-9 the M40403 diastereomers are prepared by template cyclization, followed by reduction with sodium borohydride.

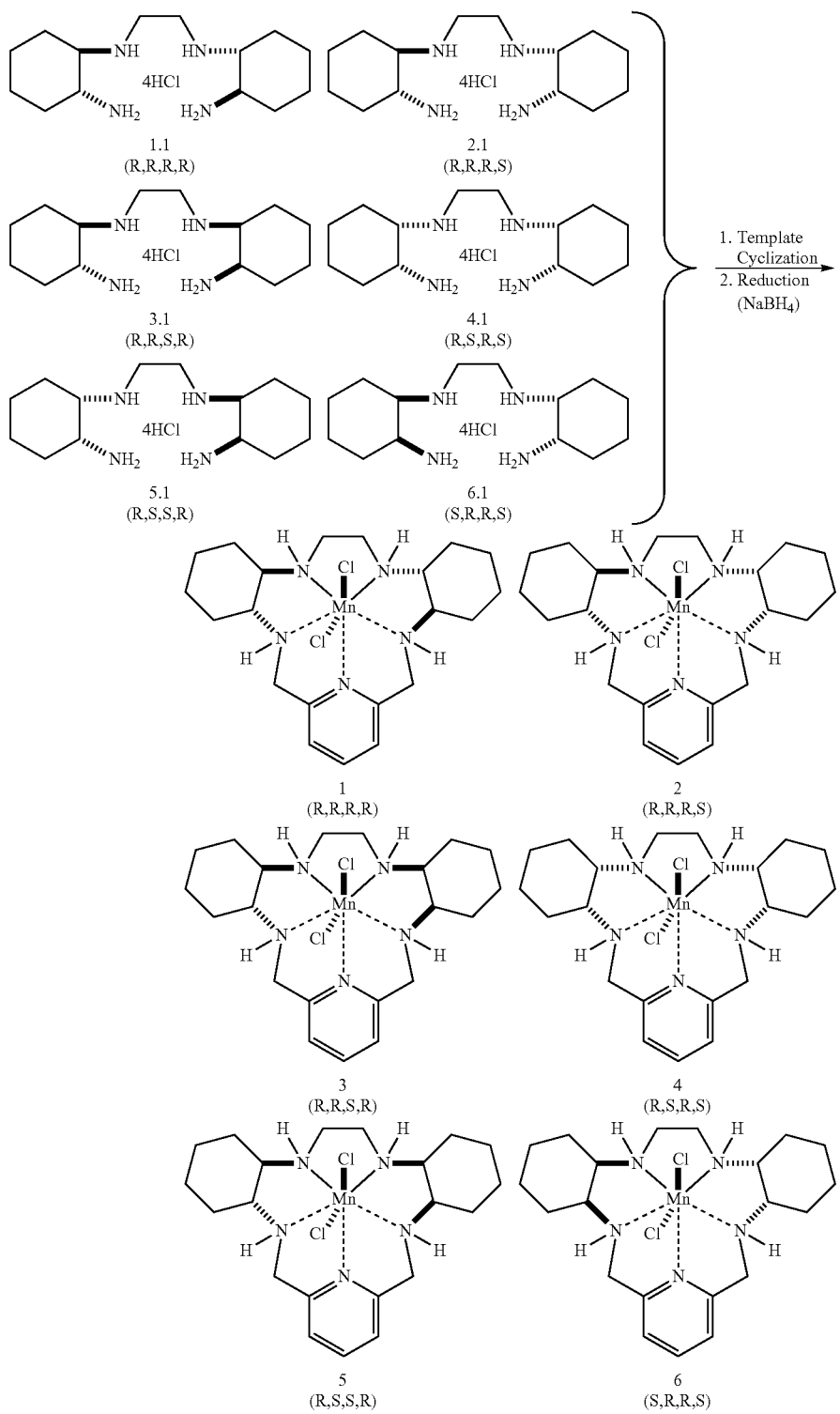

Scheme 8

Scheme 9
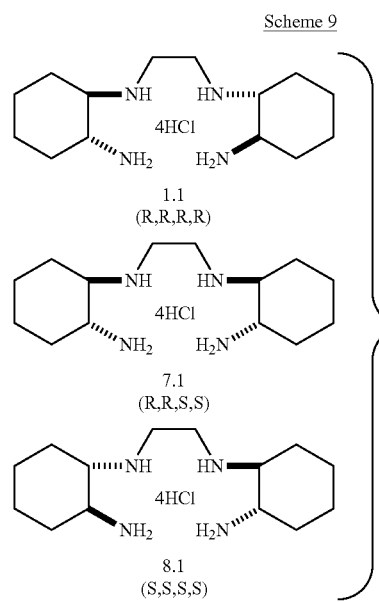
Scheme 10
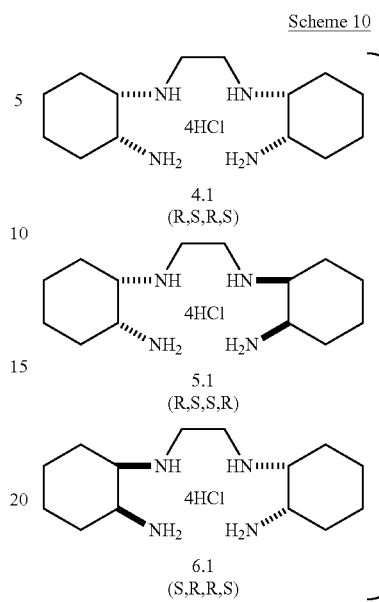
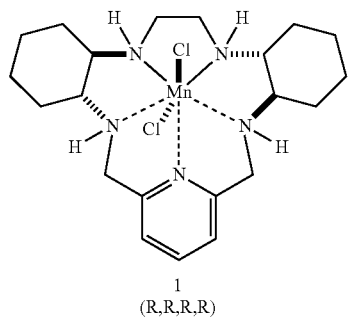
1
(R,R,R,R)
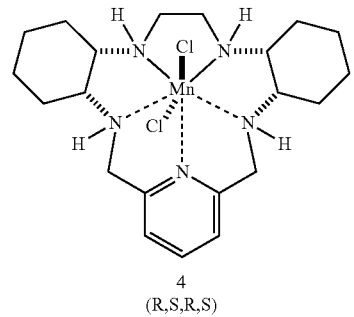
4
(R,S,R,S)
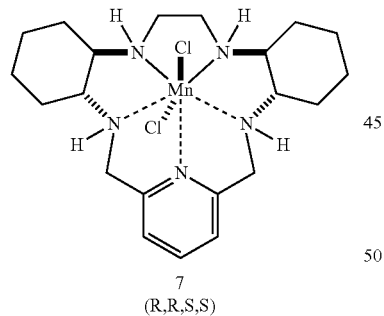
7
(R,R,S,S)
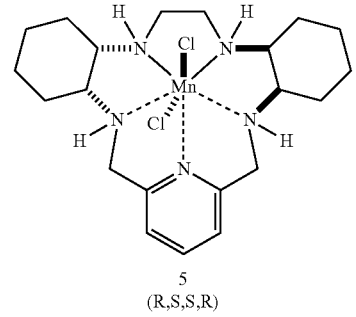
5
(R,S,S,R)
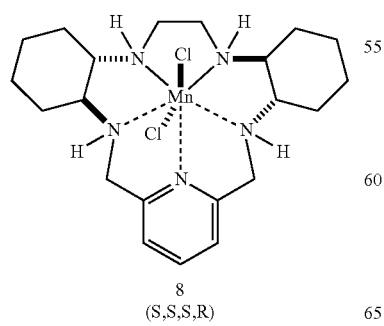
8
(S,S,S,R)
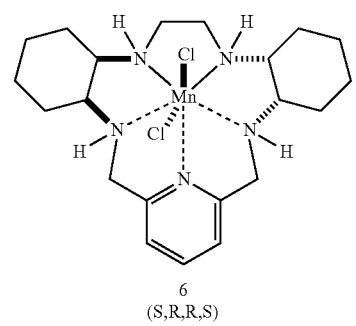
6
(S,R,R,S)

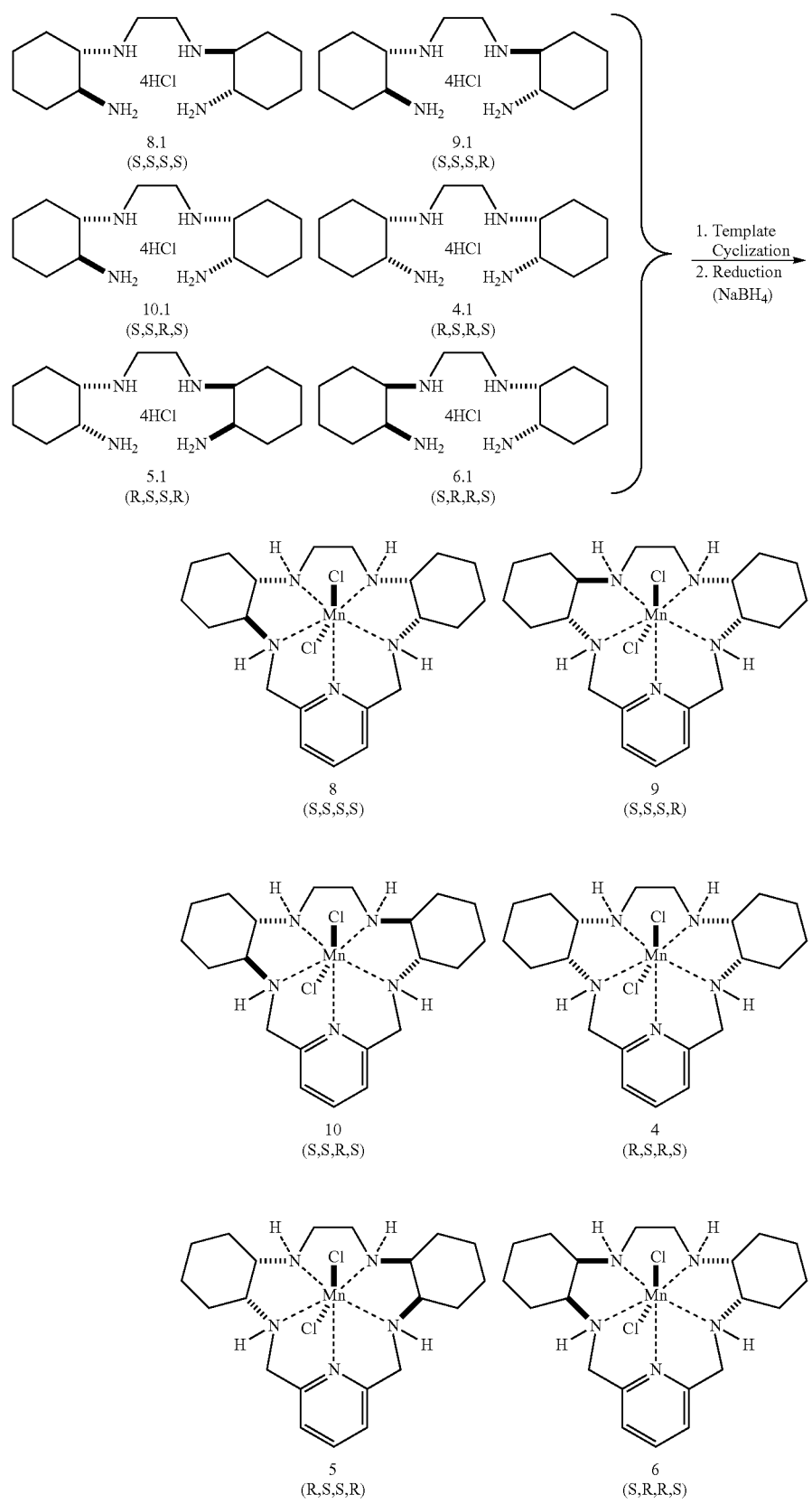

TABLE 1

Table 1. M40403 Stereoisomer Mixtures

| Compound | | ID | Enantiomeric Relation | Predicted HPLC Chromatogram |
|---|---|---|---|---|
| SET 1 | | | | SET 1 |
| | | 1 | 1 and 8 | |
| R,R, + R,S | R,R,R,R = S,R,R,R | 2 | 2 and 9 | 5 peaks |
| | R,R,S,R = R,S,R,R | 3 | 3 and 10 | (3 single stereoisomers, |
| | R,S,R,S = S,R,S,R | 4 | 4 - meso | 1 meso isomer, |
| | R,S,S,R | 5 | 5 and 6 | 1 pair of enantiomers) |
| | S,R,R,S | 6 | | |
| SET 2 | | | | SET 2 |
| | R,R,R,R | 1 | | 2 peaks |
| R,R + S,S | R,R,S,S = S,S,R,R | 7 | 7 - meso | (1 pair of enantiomers, |
| | S,S,S,S | 8 | | 1 meso isomer) |
| SET 3 | | | | SET 3 |
| | R,S,R,S = S,R,S,R | 4 | | 2 peaks |
| R,S + R,S | R,S,S,R | 5 | | (1 meso isomer, |
| | S,R,R,S | 6 | | 1 pair of enantiomers) |
| SET 4 | | | | SET 4 |
| | S,S,S,S | 8 | | 5 peaks |
| S,S + R,S | S,S,S,R = R,S,S,S | 9 | | (3 single stereoisomers, |
| | S,S,R,S = S,R,S,S | 10 | | 1 meso isomer, |
| | R,S,R,S = S,R,S,R | 4 | | 1 pair of enantiomers) |
| | R,S,S,R | 5 | | |
| | S,R,R,S | 6 | | |

4 CHIRAL CARBON CENTERS = $2^4$ = 16 THEORETICAL STEREOISOMERS DUE TO THE $C_2$ SYMMETRY OF THE MOLECULE - 10 STEREOISOMERS POSSIBLE
4 PAIRS IN ENATIOMERIC RELATION AND 2 MESO ISOMERS
HPLC (Regular): SET 1 and SET 4 - the same chromatography profile (number peaks and retention times)
SET 1 minus SET 3 - isomers with one S chiral center can be assigned Part B Separation of Stereoisomer Mixtures Chemicals, Materials, and Methods Tetrabutylammonium chloride hydrate (98%, 34, 585-7) was purchased from Aldrich Chemical Company. Sodium chloride (99.6%, S-9888) was purchased from Sigma Chemical Company. All other solvents (HPLC-grade unless otherwise indicated) and reagents were purchased from Fisher Scientific and were of the finest grade available. The SymmetryShield® $RP_{18}$ column (4.6 mm×250 mm, 5 μm particle size) and its corresponding guard column were purchased from Waters Corporation.

Reversed-Phase HPLC Experiments

Preparation of Standard Solutions

HPLC Mobile phase A was an aqueous solution consisting of 0.125 M tetrabutylammonium chloride (TBAC) and 0.5 M LiCl, prepared by adding tetrabutylammonium chloride hydrate (36.99 g) and solid LiCl (21.2 g) to a 1 L volumetric flask, diluting to volume with Millipore water, and inverting the flask several times to obtain a homogeneous solution. The resulting solution was filtered through a 0.45 μm nylon filter prior to use. Mobile phase B was HPLC-grade acetonitrile. Samples of each diastereoisomer set for HPLC-UV analysis were prepared at concentrations of ~3.0 mg/mL in a 50:50 mixture of 0.5 M LiCl in MeOH: Mobile Phase A.

Chromatographic Conditions

The column used for the HPLC experiments was the SymmetryShield $RP_{18}$ Column®, 4.6 mm×250 mm, 5 μm particle size (Waters Corporation). Separations were achieved under isocratic flow conditions using a mobile phase composed of 95% Mobile Phase A and 5% Acetonitrile (Mobile Phase B on a dual pump system). The flow rate was 1.0 mL/min. using a 15 minute runtime, and the wavelength for detection was 265 nm. The injection volume of each sample was 20 μL.

FIG. 12 contains the chromatograms resulting from the HPLC analysis of the diastereomeric mixtures of Set 1-4. Table 1 summarized the predicted results from the HPLC analysis of the diastereomeric mixtures of Set 1-4. The chromatogram resulting from the HPLC analysis of the Set 1 (R,R+R,S) M40403 stereoisomer mixture shows only five peaks, although there are a total of six stereoisomers produced. However, of the six stereoisomers produced, compounds 5 and 6 are enantiomerically related. As a result they have the same adsorption characteristics and they elute as one peak.

The chromatogram resulting from the HPLC analysis of the Set 2 (R,R+R,S) M40403 stereoisomer mixture shows only two peaks, although there are a total of three stereoisomers produced. Of the three stereoisomers produced, compounds 1 and 8 are enantiomerically related. As a result they have the same adsorption properties and they elute as one peak.

Similarly, the chromatogram resulting from the HPLC analysis of the Set 3 (R,S+R,S) M40403 stereoisomer mixture shows only two peaks, although there are a total of three stereoisomers produced. Of the three stereoisomers produced, compounds 5 and 6 are enantiomerically related and elute as one peak.

The chromatogram resulting from the HPLC analysis of the Set 4 (S,S+R,S) M40403 stereoisomer mixture shows only five peaks, although there are a total of six stereoisomers produced. Of the six stereoisomers produced, compounds 5 and 6 are enantiomerically related and elute as one peak.

Example 13

The following chiral HPLC method was used to separate the all-R and all-S enantiomers M40403 and M40419:

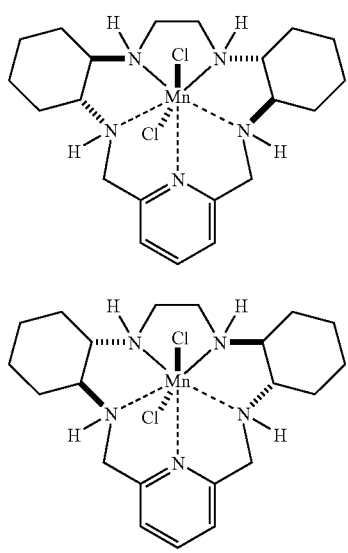

M40403

M40419

The complexes were first converted to their corresponding bis(thiocyanato) forms via ligand exchange reactions with KSCN, as shown in Scheme 10. The resultant M40403 and M40419 (SCN)$_2$ derivatives were then separated via chiral HPLC.

Scheme 12

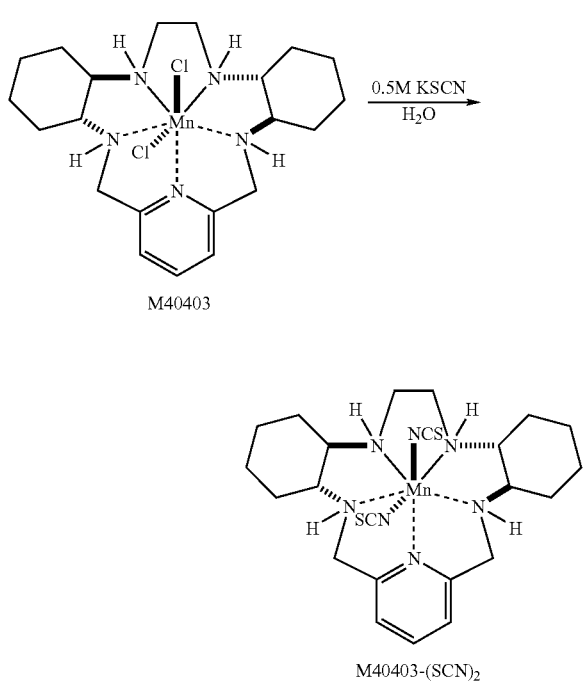

M40403

M40403-(SCN)$_2$

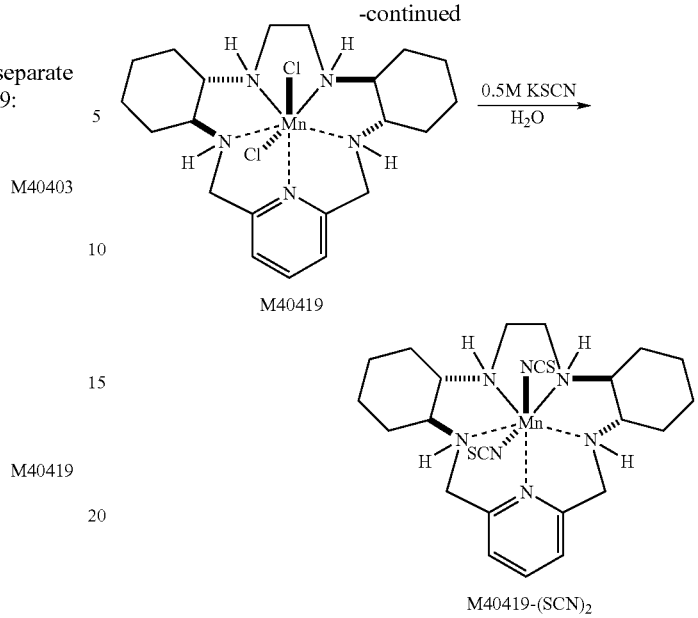

M40419

M40419-(SCN)$_2$

Chemicals, Materials, and Methods

Preparation of Bis(thiocyanato) Complexes of M40403 and M40419, respectively

M40403 (SCN)$_2$: The M40403 complex (5.0 mg, 0.01 mmol) was dissolved in 1.0 mL H$_2$O. To this solution was added KSCN (49.0 mg, 0.5 mmol) to bring its concentration to 0.5 M. A white precipitate formed immediately upon addition of the KSCN. The reaction was mixed vigorously for 60 minutes at room temperature, and the resulting suspension was extracted with CH$_2$Cl$_2$ (3×1.0 mL). The combined CH$_2$Cl$_2$ extracts were then dried over MgSO$_4$, filtered, and evaporated to yield the product as a white solid. The product was dissolved in MeOH (2.5 mL), and aliquots of the MeOH solution were mixed in a 1:1 ratio with the HPLC mobile phase (0.26 M NH$_4$SCN in MeOH) prior to injection.

M40419 (SCN)$_2$: The M40419 complex (5.0 mg, 0.01 mmol) was dissolved in 1.0 mL H$_2$O. To this solution was added KSCN (49.0 mg, 0.5 mmol) to bring its concentration to 0.5 M. A white precipitate formed immediately upon addition of the KSCN. The reaction was mixed vigorously for 60 minutes at room temperature, and the resulting suspension was extracted with CH$_2$Cl$_2$ (3×1.0 mL). The combined CH$_2$Cl$_2$ extracts were then dried over MgSO$_4$, filtered, and evaporated to yield the product as a white solid. The product was dissolved in MeOH (2.5 mL), and aliquots of the MeOH solution were mixed in a 1:1 ratio with the HPLC mobile phase (0.26 M NH$_4$SCN in MeOH) prior to injection.

Preparation of Standard Solutions

The HPLC mobile phase was a 0.2 M solution of NH$_4$SCN in MeOH, prepared by adding 2.0 g NH$_4$SCN to 100 mL MeOH(HPLC grade). The mobile phase solution was filtered through a 0.45 μm nylon filter (Osmonics) prior to use.

Chromatographic Conditions

The column used for the chiral HPLC experiment was the Chiralcel OD-RH column, 4.6 mm×150 mm, 5 μm particle size (Chiral Technologies). Separations were achieved using a simple isocratic flow at a rate of 0.5 mL/min. The wavelength for detection was 265 nm, and the injection volume of each sample was 20 μL.

The chiral HPLC profiles of the M40403 and M40419 bis(thiocyanato) enantiomers are shown in FIG. 13. The chiral HPLC profiles for the M4043-(SCN)$_2$ and M40419

(SCN)$_2$ enantiomers are shown separately in Profiles A and B. As revealed in the profiles, the all-R M40403-(SCN)$_2$ enantiomer has a retention time ($t_R$) of 6.8 min, while its all-S M40419-(SCN)$_2$ mirror-image has a retention time of 6.5 minutes. The enantiomers were then analyzed by co-injection experiment to confirm that they are truly resolved under these chromatographic conditions. The resulting HPLC profile for the co-injected enantiomers is shown in Profile C. The enantiomers were separated by approximately 0.3 minutes, thereby confirming the initial results.

What is claimed is:

1. A complex having the structure:

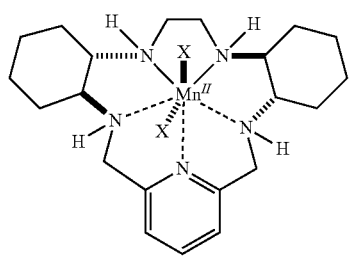

wherein X is a coordinating anion selected from the group consisting of chloride anions, thiocyanate anions, stearate anions, acetate anions, trifluoroacetate anions, carboxylate anions, formate anions and azide anions.

2. The complex of claim 1 wherein X is a chloride anion, a thiocyanate anion, or a formate anion.

3. The complex of claim 1 wherein X is a chloride anion or a thiocyanate anion.

4. A complex having the structure:

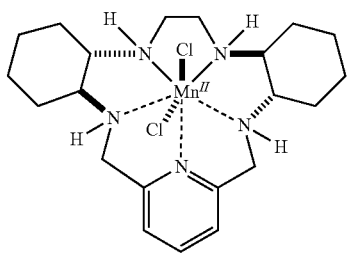

5. A complex having the structure:

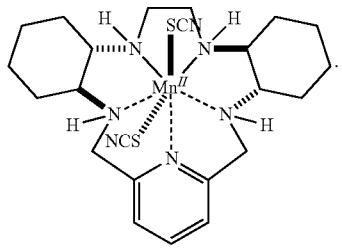

6. A composition containing a single species of a Mn$^{II}$(1,4,7,10,13-pentaazacyclopentadecane) complex corresponding to the formula:

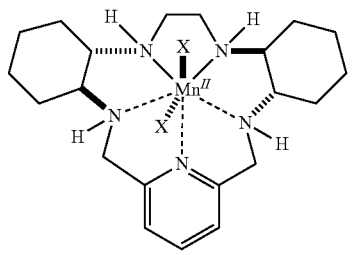

wherein X is a coordinating anion selected from the group consisting of chloride anions, thiocyanate anions, stearate anions, acetate anions, trifluoroacetate anions, carboxylate anions, formate anions and azide anions.

7. The composition of claim 6, wherein the composition is an HPLC chromatographic eluent comprising the single species of the Mn$^{II}$(1,4,7,10,13-pentaazacyclopentadecane) complex.

8. The composition of claim 6 wherein X is a chloride anion, a thiocyanate anion, or a formate anion.

9. The composition of claim 6 wherein X is a chloride anion or a thiocyanate anion.

10. The composition of claim 6 wherein the Mn$^{II}$(1,4,7,10,13-pentaazacyclopentadecane) complex has the formula:

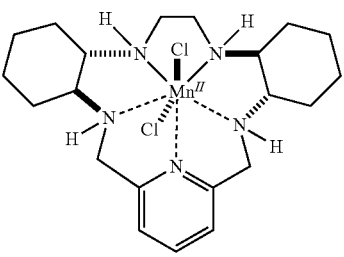

11. The composition of claim 6 wherein the Mn$^{II}$(1,4,7,10,13-pentaazacyclopentadecane) complex has the formula:

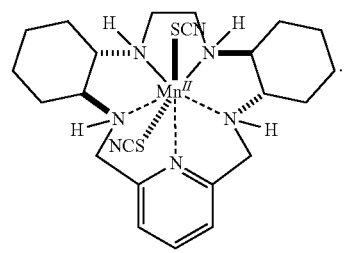

* * * * *